United States Patent [19]

Smith et al.

[11] Patent Number: 5,001,259

[45] Date of Patent: Mar. 19, 1991

[54] METHANOL CARBONYLATION PROCESS

[75] Inventors: Brad L. Smith, Portland; G. Paull Torrence, Corpus Christi; Adolfo Aguilo', Corpus Christi; James S. Alder, Corpus Christi, all of Tex.

[73] Assignee: Hoechst Celanese Corporation, Somerville, N.J.

[21] Appl. No.: 870,267

[22] Filed: Jun. 3, 1986

Related U.S. Application Data

[63] Continuation-in-part of Ser. No. 699,525, Feb. 8, 1985, abandoned, which is a continuation-in-part of Ser. No. 606,730, May 3, 1984, abandoned.

[51] Int. Cl.$^5$ .................... C07C 51/12; C07C 53/08
[52] U.S. Cl. .................................. 562/519; 562/607
[58] Field of Search .................................. 562/519

[56]         References Cited
       U.S. PATENT DOCUMENTS 3,769,329  10/1973  Paulik et al. .................... 560/232

FOREIGN PATENT DOCUMENTS 90443   10/1983  European Pat. Off. ............ 562/579
55618    4/1985  European Pat. Off. .
6054334  9/1983  Japan .

*Primary Examiner*—Vivian Garner
*Attorney, Agent, or Firm*—Ralph M. Pritchett; Donald R. Cassady

[57]              ABSTRACT

An alcohol such as methanol is reacted with carbon monoxide in a liquid reaction medium containing a rhodium catalyst stabilized with an iodide salt, especially lithium iodide, along with alkyl iodide such as methyl iodide and alkyl acetate such as methyl acetate in specified proportions. With a finite concentration of water in the reaction medium the product is the carboxylic acid instead of, for example, the anhydride. The present reaction system not only provides an acid product of unusually low water content at unexpectedly favorable reaction rates but also, whether the water content is low or, as in the case of prior-art acetic acid technology, relatively high, is characterized by unexpectedly high catalyst stability; i.e., it is resistant to catalyst precipitation out of the reaction medium.

4 Claims, 25 Drawing Sheets

LiI Dependence for Methanol Carbonylation - Continuous Unit (14-15 wt% MeI, 8 wt% H₂O, 1 wt% MeOAc, LiI as Shown, Balance HOAc, 400 ppm Rh, 190°C, 28.2 atm. abs. Total Pressure)

MeOAc Dependence for Methanol Carbonylation – Continuous Unit
(14-15 wt% MeI, 15-23 wt% LiI, 400 ppm Rh, Water and MeOAc as Shown, Balance HOAc, 190°C, 28.2 atm. abs. Total Pressure)

MeI Dependence for Methanol Carbonylation – Continuous Unit
(10 wt% LiI, MeI as Shown, 4 wt% $H_2O$, 4 wt% MeOAc, Balance HOAc, 400 ppm Rh, 190°C, 28.2 atm. abs. Total Pressure)

METHANOL CARBONYLATION PROCESS

RELATED APPLICATIONS

This is a continuation-in-part of copending U.S. Pat. Application Ser. No. 699,525, filed Feb. 8, 1985, which is a continuation-in-part of U.S. Pat. Application Ser. No. 606,730, filed May 3, 1984, both now abandoned.

THE DRAWINGS

FIGS. 1-25 show interactions among the several reaction medium components, which interactions are at the heart of the present invention.

BACKGROUND OF THE INVENTION AND PERTINENT PRIOR ART

Among currently-employed processes for synthesizing acetic acid one of the most useful commercially is the carbonylation of methanol with carbon monoxide as taught in U.S. Pat. No. 3,769,329 issued to Paulik et al. on Oct. 30, 1973. The catalyst comprises rhodium, either dissolved or otherwise dispersed in the liquid reaction medium or else supported on an inert solid, along with a halogen-containing catalyst promoter as exemplified by, for example, methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. These compounds are employed as promoters, not stabilizers. Most typically and usefully, the reaction is conducted with the catalyst being dissolved in a liquid reaction medium through which carbon monoxide gas is continuously bubbled.

Paulik et al. teach that the liquid reaction medium can be any solvent compatible with the catalyst system and that it may comprise, for example, the pure alcohol which is being reacted, or mixtures thereof with the desired carboxylic acid end product and/or esters of these two compounds. However, the patentees teach further that the preferred solvent and liquid reaction medium for the process is the desired carboxylic acid itself, i.e., acetic acid when methanol is being carbonylated to produce acetic acid.

An important aspect of the teachings of Paulik et al. is that water should also be present in the reaction mixture in order to attain a satisfactorily high reaction rate. The patentees exemplify a large number of reaction systems including a large number of applicable liquid reaction media. The general thrust of their teachings is, however, that a substantial quantity of water helps in attaining an adequately high reaction rate. The patentees teach furthermore that reducing the water content leads to the production of ester product as opposed to carboxylic acid. Considering specifically the carbonylation of methanol to acetic acid in a solvent comprising predominantly acetic acid and using the promoted catalyst taught by Paulik et al., it is taught in European Patent Application No. 0055 618 that typically about 14-15 wt % water is present in the reaction medium of a typical acetic acid plant using this technology. It will be seen that in recovering acetic acid in anhydrous or nearly anhydrous form from such a reaction solvent, separating the acetic acid from this appreciable quantity of water, involves substantial expenditure of energy in distillation and/or additional processing steps such as solvent extraction, as well as enlarging some of the process equipment as compared with that used in handling drier materials. Also Hjortkjaer and Jensen [Ind. Eng. Chem., Prod. Res. Dev. 16, 281-285 (1977)] have shown that increasing the water from 0 to 14 wt % water increases the reaction rate of methanol carbonylation. Above 14 wt % water the reaction rate is unchanged.

In addition, as will be further explained hereinbelow, the catalyst tends to precipitate out of the reaction medium as employed in the process of Paulik et al., especially during the course of distillation operations to separate the product from the catalyst solution when the carbon monoxide content of the catalyst system is reduced (EP0055618). It has now been found that this tendency increases as the water content of the reaction medium is decreased. Thus, although it might appear obvious to try to operate the process of Paulik et al. at minimal water concentration in order to reduce the cost of handling reaction product containing a substantial amount of water while still retaining enough water for adequate reaction rate, the requirement for appreciable water in order to maintain catalyst activity and stability works against this end.

Other reaction systems are known in the art in which an alcohol such as methanol or an ether such as dimethyl ether can be carbonylated to an acid or ester derivative using special solvents such as aryl esters of the acid under substantially anhydrous reaction conditions. The product acid itself can be a component of the solvent system. Such a process is disclosed in U.S. Pat. No. 4,212,989 issued Jul. 15, 1980 to Isshiki et al., with the catalytic metal being a member of the group consisting of rhodium, palladium, iridium, platinum, ruthenium, osmium, cobalt, iron, and nickel. A somewhat related patent is U.S. Pat. No. 4,336,399 to the same patentees, wherein a nickel-based catalyst system is employed. Considering U.S. Pat. No. 4,212,989 in particular, the relevance to the present invention is that the catalyst comprises both the catalytic metal, as exemplified by rhodium, along with what the patentees characterize as a promoter, such as the organic iodides employed by Paulik et al. as well as what the patentees characterize as an organic accelerating agent. The accelerating agents include a wide range of organic compounds of trivalent nitrogen, phosphorus, arsenic, and antimony. Sufficient accelerator is used to form a stoichiometric coordination compound with the catalytic metal. Where the solvent consists solely of acetic acid, or acetic acid mixed with the feedstock methanol, only the catalyst promoter is employed (without the accelerating agent), and complete yield data are not set forth. It is stated, however, that in this instance "large quantities" of water and hydrogen iodide were found in the product, which was contrary to the intent of the patentees.

European Published Patent Application No. 0 055 618 to Monsanto Company discloses carbonylation of an alcohol using a catalyst comprising rhodium and an iodine or bromine component wherein precipitation of the catalyst during carbon monoxide-deficient conditions is alleviated by adding any of several named stabilizers. A substantial quantity of water, of the order of 14-15 wt %, was employed in the reaction medium. The stabilizers tested included simple iodide salts, but the more effective stabilizers appeared to be any of several types of specially-selected organic compounds.

There is no teaching that the concentrations of methyl acetate and iodide salts are significant parameters in affecting the rate of carbonylation of methanol to produce acetic acid especially at low water concentrations. When an iodide salt is used as the stabilizer, the amount used is relatively small and the indication is that the primary criterion in selecting the concentration of iodide salt to be employed is the ratio of iodide to rhodium. That is, the patentees teach that it is generally preferred to have an excess of iodine over the amount of iodine which is present as a ligand with the rhodium component of the catalyst. Generally speaking the teaching of the patentees appears to be that iodide which is added as, for example, an iodide salt functions simply as a precursor component of the catalyst system. Where the patentees add hydrogen iodide, they regard it as a precursor of the promoter methyl iodide. There is no clear teaching that simple iodide ions as such are of any significance nor that it is desirable to have them present in substantial excess to increase the rate of the reaction. As a matter of fact Eby and Singleton [*Applied Industrial Catalysis*, Vol. 1, 275–296(1983)] from Monsanto state that iodide salts of alkali metals are inactive as cocatalyst in the rhodium-catalyzed carbonylation of methanol.

Carbonylation of esters, such as methyl acetate, or ethers, such as dimethyl ether, to form a carboxylic acid anhydride such as acetic anhydride is disclosed in U.S. Pat. No. 4,115,444 to Rizkalla and in European Patent Application No. 0,008,396 by Erpenbach et. al. and assigned to Hoechst. In both cases the catalyst system comprises rhodium, an iodide, and a trivalent nitrogen or phosphorus compound. Acetic acid can be a component of the reaction solvent system, but it is not the reaction product. Minor amounts of water are indicated to be acceptable to the extent that water is found in the commercially-available forms of the reactants. However, essentially dry conditions are to be maintained in these reaction systems.

U.S. Pat. No. 4,374,070 to Larkins et al. teaches the preparation of acetic anhydride in a reaction medium which is, of course, anhydrous by carbonylating methyl acetate in the presence of rhodium, lithium, and an iodide compound. The lithium can be added as lithium iodide. Aside from the fact that the reaction is a different one from that with which the present invention is concerned, there is no teaching that it is important per se that the lithium be present in any particular form such as the iodide. There is no teaching that iodide ions as such are significant.

In summary, current technology in the field of carbonylating an alcohol such as methanol to form a carboxylic acid such as acetic acid still lacks a simple method for maintaining a highly stable catalyst system and for attaining industrially attractive conversion rates under conditions of low water content in the liquid reaction medium whereby the expense and capital investment costs of recovering the acid product with a very low water content can be minimized.

It is, accordingly, an object of the present invention to provide a reaction system with which an alcohol, as exemplified by methanol, can be carbonylated to a carboxylic acid derivative such as acetic acid while using a liquid reaction medium having a lower water content than heretofore considered feasible. It is another object to provide a catalyst system which, regardless of the water content of the reaction medium, will be of improved stability—i.e., more resistant to precipitation of solid catalyst therefrom. It is also a related object to provide a catalyst system characterized by a substantial reduction in the undesired formation of by-product propionic acid, carbon dioxide, and hydrogen as compared with high water systems used in the prior art. Other objects will be apparent from the following detailed description.

BRIEF SUMMARY OF THE INVENTION

Broadly, the invention is an improvement in the prior-art rhodium-catalyzed carbonylation of an alcohol to produce the carboxylic acid having one carbon atom more than the alcohol. In particular, the invention is directed to producing acetic acid (HOAc) from methanol (MeOH). Present in the reaction medium are the ester of the alcohol being carbonylated with the acid product of the carbonylation reaction along with a halide derivative of the hydrocarbon corresponding to the alcohol, especially the iodide. Thus, in reaction systems wherein methanol is being carbonylated to acetic acid, the ester is methyl acetate (MeOAc) and the halide is a methyl halide, especially methyl iodide (MeI). Rhodium is present in catalytically-effective concentration.

The invention resides primarily in the discovery that catalyst stability and the productivity of the carbonylation reactor can be maintained at surprisingly high levels, even at very low water concentrations in the reaction medium (despite the general industrial practice of maintaining approximately 14 wt % or 15 wt % water) as discussed in EP0055618 by maintaining in the reaction medium, along with a catalytically-effective amount of rhodium, at least a finite concentration of water (which can, however, be unexpectedly low as just explained) along with methyl acetate and methyl iodide when making acetic acid in specified proportions while there is also maintained in the reaction medium a specified concentration of iodide ions. The iodide ion, which is over and above the iodide which is present as methyl iodide or other organic iodide, is present as a simple salt, with lithium iodide being preferred. However, any iodide salt which is soluble in the reaction medium in effective concentration at the reaction temperature can be employed. No special ligands, as exemplified by, for example, phosphines, are needed.

Although the invention is broadly as just described, its preferred embodiments lie also in the discovery that there is an interaction between the iodide salt and the ester, especially at low water concentrations. That is, optimal results are obtained when each of these named components is present in certain specified concentrations. Generally speaking, the iodide salt is employed in concentrations which are higher than would be suggested by the known prior art as being needed. By using relatively high concentrations of the iodide salt and the methyl ester of the acid being synthesized, one obtains a surprising degree of catalyst stability and reactor productivity even when the liquid reaction medium contains water in concentrations as low as about 0.1 wt %, so low that it can broadly be defined simply as "a finite concentration" of water. The known prior art would suggest that operation under such low-water conditions would result in little or no formation of acetic acid. Furthermore, it has now been found that the stability of the rhodium catalyst would be very poor, especially during the product-recovery steps of the process wherein distillation for the purpose of recovering the acetic acid product tends to remove from the catalyst the carbon monoxide which, in the environment maintained in the reaction vessel itself, is a ligand with stabilizing affect on the rhodium.

DETAILED DESCRIPTION AND PREFERRED EMBODIMENTS

Figure 1:
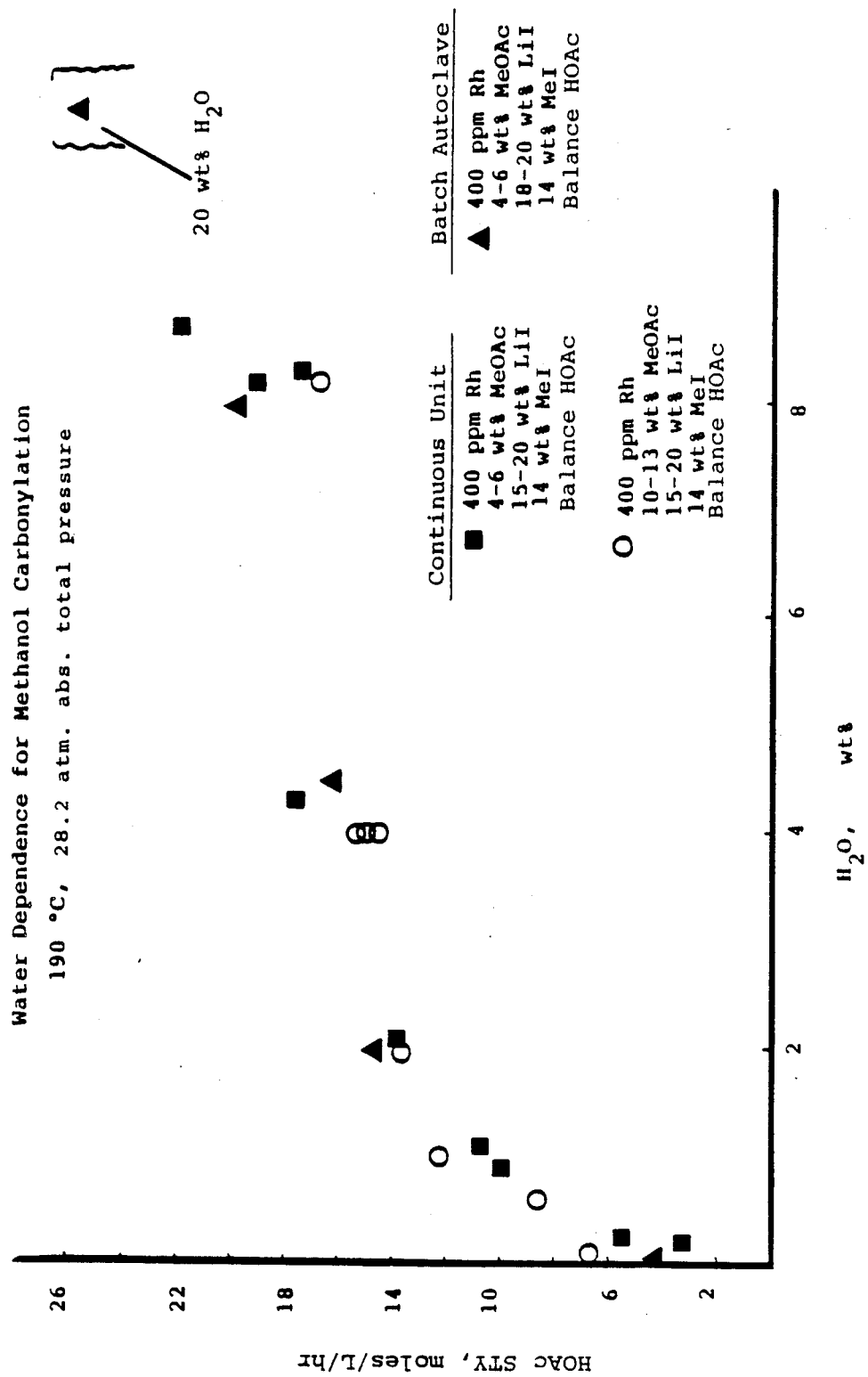

The following description is directed to the carbonylation of methanol to produce acetic acid. However, as previously explained, the technology is applicable to the carbonylation of higher homologues of methanol to form acids which are the higher homologues of acetic acid.

A reaction system which can be employed, within which the present improvement is used with no changes except for the adjustment of the composition of the liquid reaction medium which will be further explained below, comprises (a) a liquid-phase carbonylation reactor, (b) a so-called "flasher", and (c) a "methyl iodide-acetic acid splitter column". The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. Alternate distillation systems can be employed so long as they provide means for recovering the crude acetic acid and recycling to the reactor catalyst solution, methyl iodide, and methyl acetate. Carbon monoxide is continuously introduced into the carbonylation reactor just below the agitator which is used to stir the contents. The carbon monoxide is, of course, thoroughly dispersed through the reacting liquid by this means. A gaseous purge stream is vented from the head of the reactor to prevent buildup of gaseous by-products and to maintain a set carbon monoxide partial pressure at a given total reactor pressure. The temperature of the reactor is controlled automatically, and the carbon monoxide is introduced at a rate sufficient to maintain a constant total reactor pressure. The carbon monoxide partial pressure in the reactor is typically about 2 to 30 atmospheres absolute, preferably about 4 to 15 atmospheres absolute. Because of the partial pressure of by-products and the vapor pressure of the contained liquids, the total reactor pressure is from about 15 to 45 atmospheres absolute, with the reaction temperature being approximately 150° to 250° C. Preferably, the reactor temperature is about 180° to 220° C.

Liquid product is drawn off from the carbonylation reactor at a rate sufficient to maintain a constant level therein and is introduced to the flasher at a point intermediate between the top and bottom thereof. In the flasher the catalyst solution is withdrawn as a base stream (predominantly acetic acid containing the rhodium and the iodide salt along with lesser quantities of methyl acetate, methyl iodide, and water), while the overhead of the flasher comprises largely the product acetic acid along with methyl iodide, methyl acetate, and water. A portion of the carbon monoxide along with gaseous by-products such as methane, hydrogen, and carbon dioxide exits the top of the flasher.

The product acetic acid drawn from the base of the methyl iodide-acetic acid splitter column (it can also be withdrawn as a side stream near the base) is then drawn off for final purification as desired by methods which are obvious to those skilled in the art and which are outside the scope of the present invention. The overhead from the methyl iodide-acetic acid splitter, comprising mainly methyl iodide and methyl acetate, is recycled to the carbonylation reactor along with fresh methyl iodide, the fresh methyl iodide being introduced at a rate sufficient to maintain in the carbonylation reactor the desired concentration of methyl iodide in the liquid reaction medium. The fresh methyl iodide is needed to compensate for losses in the flasher and carbonylation reactor vent streams.

The primary reaction control method comprises continually analyzing the liquid contents of the reactor as well as the carbon monoxide content of the gas in the reactor head space and, on the basis of these analyses, controlling the flow of carbon monoxide, water, methanol, and methyl iodide to maintain the specified reaction medium composition. It should be further explained that the methanol addition to the carbonylation reactor is based not on an analysis of its contents for methanol but, rather, on analysis for methyl acetate content. Most of the methanol is converted almost immediately to methyl acetate when it enters the carbonylation reactor.

There are two criteria which need to be satisfied to maintain optimal performance of the system just described. This is over and above the maintenance of a stable catalyst system from which the rhodium catalyst does not precipitate during the course of the flasher operation.(As previously explained, this is a problem recognized by the prior art although the prior art has not employed the presently-described means for addressing it.) First, it is desired to maintain a high productivity in the carbonylation reactor itself, as measured by the quantity of acetic acid formed per unit time per unit volume or weight of liquid reaction medium contained in the reactor. This might be termed "reactor productivity" or "reactor space-time yield". Here again the art as it presently exists recognizes the need to maintain reactor productivity although it has not taught the presently-described methods for attaining this end.

Second, the present process improvement contemplates the maintenance of optimal productivity, as measured by the ultimately-recovered concentrated acetic acid in the combined system including both the carbonylation reactor and the product recovery system. Although the details of the product recovery system, including the methyl iodide-acetic acid splitter or its equivalent, are not directly relevant to the present disclosure, it will be recognized by anyone skilled in the art that water is an undesirable component of the crude acetic acid and that the more water there is in this stream the greater will be the operating costs and required capital investment in the product recovery-purification system. Thus, there is also a "system productivity" to be considered in addition to the "reaction productivity", with the "system productivity" depending upon the degree to which water is kept out of the residue of the methyl iodide-acetic acid splitter column. The dryer this stream is, the higher will be the over-all system productivity so long as reaction productivity is maintained.

The present process improvement is directed at maintaining both an optimal reactor productivity and also an optimal over-all system productivity. Fundamentally, the current state of the art seems to be resigned to accepting a relatively high water content in the liquid reaction medium with a resulting undesirably high water content in the crude acetic acid initially recovered from the reaction and primary product recovery system as just described.

As previously explained, the rate of the carbonylation reaction according to the present state of the art has been highly dependent on water concentration in the reaction medium as taught by U.S. Pat. No. 3,769,329; EP0055618; and Hjortkjaer and Jensen(1977). That is, as the water concentration is reduced below about 14-15 wt % water, the rate of reaction declines. The catalyst also becomes more susceptible to inactivation and precipitation when it is present in process streams of low carbon monoxide partial pressures. It has now been discovered, however, that increased acetic acid-production capacity can be achieved at water concentrations below about 14 wt % (at water contents above about 14 wt %, the reaction rate is not particularly dependent on water concentration) by utilizing a synergism which exists between methyl acetate and the iodide salt as exemplified by lithium iodide especially at low water concentrations. This effect is illustrated in Table I below, which summarizes the results of five pilot plant runs in which the contents of the reaction medium were varied as shown with the reactor space-time yield which was attained being the criterion for measuring efficacy of the catalyst system which was used. In each case the space-time yield (STY) as listed is expressed in gram—moles of acetic acid produced per hour per liter of reaction medium contained in the carbonylation reactor, the volume of reaction medium being taken at ambient temperature and in the unaerated state. The pilot plant was operated in the manner previously described—that is, there was a stirred autoclave followed by two product recovery system distillation steps, and the process control scheme was as described also hereinabove. The reactor temperature in all cases was between about 190° C. and 195° C. Total reactor pressure was approximately 28 atmospheres absolute, with the carbon monoxide partial pressure being approximately 8-12 atmospheres absolute. In each case the balance of the liquid reaction medium, not specifically listed in the table, was acetic acid. Minor quantities of other components were present, of course. Because the reaction rate is directly proportional to the rhodium concentration, and to facilitate the comparison of the different runs, the STY in the runs discussed hereinbelow has been normalized to 400 ppm rhodium unless otherwise indicated explicitly.

content with the water being still at the low level of 4 wt % brought the STY up to a level higher than that obtained in Run (b). In Run (e), with the water still being at the relatively low level of 4 wt %, an increase in both lithium iodide and methyl acetate brought the STY up to 15.8, essentially the same STY as for Run (a) in which a high water content was employed.

The conclusion from the foregoing comparative experiments is that under low water concentrations methyl acetate and lithium iodide act as rate promoters only when relatively high concentrations of each of these components are present and that the promotion is higher when both of these components are present simultaneously. This has not been recognized in the prior art. It will be seen also that the concentration of lithium iodide was quite high as compared with what little prior art there is dealing with the use of halide salts in reaction systems of this sort.

It has now also been discovered that in runs involving methyl acetate concentration greater than about 2 wt %, lithium iodide is necessary not only to increase the reaction rate but also to stabilize the rhodium catalyst due to the deleterious effect of high methyl acetate concentrations on its stability, even at high water concentrations. For example, in experimentation carried out at 200° C. with 14 wt % water in the reaction medium along with 15 wt % methyl iodide and no lithium iodide and using 320-240 ppm of rhodium as the catalyst, the rhodium precipitation loss was found to be about 12 ppm of rhodium concentration per hour at an average concentration of 2 wt % methyl acetate in the reaction medium whereas, with other reaction components being substantially unchanged, the rhodium loss was 1.3 ppm per hour or lower when the methyl acetate content was only about 1 wt %. This exemplifies again that the reaction-accelerating effect of methyl acetate is best realized in conjunction with a relatively high concentration of iodide salt. This has not been recognized in the prior art.

Some runs were made in which the reaction was carried out in a batch autoclave instead of the continuously-operating pilot plant reaction system as described above. In these runs an autoclave of suitably corrosion-resistant metal was charged with rhodium triiodide (typically between 200 and 500 ppm rhodium content in the resulting mixture), 14 to 19 wt % methyl iodide, water in the concentration that was to be tested, vari-

TABLE I

| | GENERAL CONDITIONS | | | | |
| --- | --- | --- | --- | --- | --- |
| REAGENTS | Run (a) High Water No LiI Low MeOAc | Run (b) Low Water Low LiI Low MeOAc | Run (c) Low Water No LiI High MeOAc | Run (d) Low Water High LiI Low MeOAc | Run (e) Low Water High LiI High MeOAc |
| Water, wt % | 14 | 4 | 4 | 4 | 4 |
| MeOAc, wt % | 1 | 1-1.5 | 4 | 1 | 4 |
| LiI, wt % | 0 | 2.5 | 0 | 20 | 20 |
| Rh, ppm | 400 | 400 | 400 | 400 | 400 |
| MeI, wt % | 14 | 13-15 | 14 | 14 | 13.5 |
| STY | 16.9 | 5.2 | 10.4 | 11.0 | 15.8 |

From inspection of the foregoing tabulation it will be seen that Run (a), with a high water content typical of the prior art, had an STY of 16.9. In Run (b), with water content reduced to 4 wt % with methyl acetate being slightly increased but with the other components being essentially unchanged, an STY of only 5.2 was obtained. In Run (c) with low water, no lithium iodide, elevated methyl acetate, and unchanged methyl iodide, the STY was only 10.4. In Run (d), increasing the lithium iodide able amounts of the stabilizer which was to be tested, 15 ml of methanol, and 40 to 60 grams of acetic acid. The autoclave was sealed, pressured to approximately 28.2 atmospheres absolute of carbon monoxide partial pressure and pressure checked at 25° C. After this the autoclave was slowly vented of its carbon monoxide content and then flushed two times with 4.4 atmospheres absolute of carbon monoxide. The autoclave was then pressured to 11.2 atmospheres absolute with carbon monoxide and heated to 185° C. to 190° C., after which the agitator with which the autoclave was provided was turned on. The autoclave was then further pressured with carbon monoxide to 28.4 atmospheres absolute, and the rate of reaction was determined by monitoring the amount of carbon monoxide consumed over a period of time while assuming that the ideal-gas law applied to carbon monoxide. Reaction rate was determined from plots of carbon monoxide uptake versus time, the resulting data then being converted to the carbonylation reaction rate assuming ideal gas behavior for the carbon monoxide. This procedure was generally used in studying the effect of using as reaction stabilizer several iodide salts, some of which had organic cations.

Using both the continuous pilot plant and also the batch reaction system as just described, it has now been determined that the interaction between water content, iodide salt, methyl acetate, and methyl iodide is as set forth in the following tabulation, in which there are set forth both a broad range and a preferred, or optimal, range for obtaining both catalyst stabilization and reaction rate enhancement. The "preferred" range is that which is preferred from the standpoint of optimal performance of the entire system including the primary product recovery system as explained hereinabove. It will be seen that the recommended concentrations are the same for both stabilization and also rate enhancement with one exception: the exception is that the "preferred" range for methyl acetate is 0.5–5 wt % for catalyst stabilization whereas it is 2–5 wt % for optimal rate enhancement. Broadly, of course, this means that in either case a range between 0.5 wt % and 5 wt % would be satisfactory, but that, depending upon whether it is catalyst stabilization or maximal rate enhancement that one aims to maximize in a given plant operating situation, the bottom end of the desired methyl acetate range is slightly higher when maximal rate enhancement is being sought.

TABLE II

| | Stabilization | | RATE ENHANCEMENT | |
|---|---|---|---|---|
| | Broad wt % (1) | Preferred wt % | Broad wt % (1) | Preferred wt % |
| H₂O | 0.1–20 | 1–4 | 0.1–20 | 1–4 |
| Inorganic Iodide (as LiI) | 2–20 | 10–20 | 2–20 | 10–20 |
| MeOAc | 0.5–30 | 0.5–5 | 0.5–30 | 2–5 |
| MeI | 5–20 | 12–16 | 5–20 | 12–16 |
| HOAc | Balance | Balance | Balance | Balance |
| Rh (ppm) | 200–1000 | 300–600 | 200–1000 | 300–600 |

(1) Particular utility obtains at about 0.1–14%, water content being a more significant factor below about 14 wt %.

To reiterate what has been said hereinabove, water contents below about 14% are low as compared with prior art, and the iodide salt content here is quite high. The upper end of the recommended methyl acetate concentration is also higher than one can calculate as being present in a simulated commercial catalyst solution (EP No. 0055618).

The interrelationship between lithium iodide concentration and water content in the reaction medium was investigated in a series of batch runs in which lithium iodide content in the reaction medium was varied between about 0.0 molar and about 1.5 molar (20 wt %) with 2 wt % water in the reaction medium, the results so obtained being compared with those obtained with 14 wt % water in the medium. Methyl iodide concentration was 14 wt %, reaction temperature was 190° C., and rhodium content of the reaction medium was 472 ppm. The initial methyl acetate content was 27 wt % in these batch runs. In continuous operation it would be much lower. With 14 wt % water, the space-time yield declined, as the lithium iodide content declined, from about 20 moles per liter per hour at about 1.5 molar (20 wt %) lithium iodide concentration down to about 12 to 13 moles per liter per hour with a lithium iodide molar concentration of about 0.8 (11 wt %). There was some scatter of data points, and with no lithium iodide at all, the space-time yield was indicated to be about 13. The curves of rate versus lithium iodide concentration were not as well defined at high water as at 2 wt % water.

With 2 wt % water, the effect of lithium iodide was pronounced. At around 0.2 molar (2.7 wt %) lithium iodide, the space—time yield was 7 moles per liter per hour, and this increased with lithium iodide increase in a very nearly linear fashion to a space-time yield of about 21 moles per liter per hour when the lithium iodide concentration was about 1.5 molar (20 wt %). Thus, by increasing lithium iodide content it was possible to obtain substantially the same space-time yield at 2 wt % water as at 14 wt % water with a pronounced resulting enhancement of the ability of the plant to operate under desirable conditions of low water content.

The interrelation between methyl acetate and lithium iodide content was investigated in three sets of batch runs in which, at a constant lithium iodide content in each case, the methyl acetate content of the reaction medium was varied from 0 to a maximum of about 3.0 molar (33 wt %). In all cases the methyl iodide content was 14 wt %, the water content was 2 wt %, the temperature was 190° C., and the rhodium content was 236 ppm. When the lithium iodide content was 0.17 molar (2.5 wt %), the space-time yield increased gradually from 0 when no methyl acetate was present up to about 7 moles per liter per hour when the methyl acetate content was about 26 wt %. Plotted on rectangular coordinates, the curve was gently convex upward. When the lithium iodide content was 1.5 molar (20 wt %), the space-time yield increased from 0 when the methyl acetate was 0 to about 14 moles per liter per hour when the methyl acetate content was about 33 wt %. That is, when the methyl acetate was about 33 wt %, the use of 1.5 molar (20 wt %) lithium iodide multiplied the space-time yield by a factor of about 2 as compared with conditions obtained when using 0.17 molar (2.5 wt %) lithium iodide.

Another series of runs was carried out to investigate the differences, if any, between lithium iodide (a representative metal iodide salt) and N-methylpicolinium iodide (NMPI), a representative salt having an organic cation. NMPI is formed by quaternizing 3-picoline with methyl iodide. The reaction medium contained the NMPI, 2 wt % water, 14.4 wt % free methyl iodide, 27 wt % methyl acetate, and the balance acetic acid. It also contained 472 ppm of rhodium. Reaction temperature was 190° C. Over a concentration range of either lithium iodide or NMPI ranging from about 0.2 molar to about 0.8 molar, a plot of reaction space-time yield against the molar concentration of either the lithium iodide or the NMPI showed that, within the limits of experimental error, there was no difference in space-time yield obtained at a given molar concentration of lithium iodide as compared with the same concentration of NMPI. It will be recognized that it is the concentration of iodide ion that is the controlling factor, and that at a given molar concentration of iodide the nature of the cation is not as significant as the effect of the iodide concentration. Any metal iodide salt, or any iodide salt of an organic cation, can be used provided that the salt is sufficiently soluble in the reaction medium to provide the desired level of the stabilizing iodide. The iodide salt can be a quaternary salt of an organic cation or the iodide salt of an inorganic cation, preferably it is an iodide salt of a member of the group consisting of the metals of Group Ia and Group IIa of the periodic table as set forth in the "Handbook of Chemistry and Physics" published by CRC Press, Cleveland, Ohio, 1975–76 (56th edition). In particular, alkali metal iodides are useful, with lithium iodide being preferred.

EXAMPLE 1

The following run was carried out in continuously-operating apparatus comprising a stirred reactor from which the product was drawn off continuously for workup in the manner previously described hereinabove. The carbonylation reactor contained approximately 1800 ml of liquid reaction medium, measured at ambient temperature in the bubble-free state. Its contents were analyzed periodically throughout the run, and these analyses were employed to control the flows of the several streams entering the reactor in such a manner as to maintain in the liquid reaction medium about 13 to 16 wt % methyl iodide, 4 to 5 wt % methyl acetate, 19 to 19.5 wt % lithium iodide, 4 to 5 wt % water, and 310 to 335 ppm of rhodium. The balance of the reaction medium was acetic acid. Before starting the run, the carbonylation reactor had been initially charged with a mixture of about 16 wt % water, 12 wt % methyl iodide, 0.7 wt % methyl acetate, and the balance acetic acid, the total mixture containing about 400 ppm of rhodium in the form of a rhodium carbonyl iodide compound. The rhodium compound can be prepared by dissolving rhodium triiodide in acetic acid containing 15–20 wt % water at about 110° C. while sparging carbon monoxide through the mixture at a pressure of about one atmosphere absolute or higher.

During operation the reactor temperature was maintained between about 189° C. and 191° C. The pressure was maintained at about 28 atmospheres absolute. Carbon monoxide was continuously introduced through a sparger situated below the agitator blades, and a continuous vent of gas was drawn off from the top of the vapor space contained in the upper part of the reactor at about 15 liters per hour (ambient temperature and pressure). The carbon monoxide partial pressure in the reactor head space was maintained at about 13 atmospheres absolute.

By means of a level control sensing the liquid level within the reactor, liquid reaction product was continuously drawn off and fed onto the tray of a single-tray flasher operating at a head pressure of about 2.4 atmospheres absolute. Of the liquid fed into the flasher, approximately 35% was distilled overhead for further redistillation in the methyl iodide-acetic acid splitter column while the remainder was drawn from the base of the column and returned to the carbonylation reactor. This stream comprised predominantly acetic acid and contained the catalyst.

The methyl iodide-acetic acid splitter column contained 20 trays, with the overhead from the flasher just described being introduced onto the 15th tray from the bottom. This splitter column was operated at a head pressure of 1 atmosphere absolute and with a reflux ratio of 1:1. Of the feed initially introduced into this column, approximately 60% was taken overhead and was recycled to the carbonylation reactor. This stream contained predominantly methyl iodide and lesser quantities of methyl acetate. Such methyl iodide makeup as was necessary to maintain the desired methyl iodide content in the carbonylation reactor was introduced into this recycling stream before it was returned to the carbonylation reactor. The rate of methyl iodide introduction was set by periodic analyses of the vent streams leaving the reactor and the flasher, enough methyl iodide being introduced to make up for these process losses. Also introduced into this stream just before entering the carbonylation reactor was sufficient methanol to maintain the desired methyl acetate content in the reactor liquid medium. (Methanol is converted almost immediately to methyl acetate upon entering the reactor). Such water as was needed to maintain the desired water content in the reactor was also introduced with this methyl iodide recycle stream.

Preferably, water recovered in any of the distillate streams is recycled to the reactor. There is very little consumption of water in the reaction. If a water phase forms at any point in the product-recovery system, it will probably contain methyl iodide, which should be returned to the reactor.

The residue stream from the methyl iodide-acetic acid splitter column was drawn off as the crude acetic acid product, to be purified further as desired by conventional methods outside the scope of the present invention. As previously explained, a primary object of the operation was to produce a crude acetic acid at this point containing only a small amount of water.

With the system operating as just described, the STY of acetic acid in the crude acetic acid product drawn from the base of the methyl iodide-acetic acid splitter was approximately 14 gram-moles of acetic acid (calculated as pure acetic acid) per hour per liter of liquid reaction medium contained in the carbonylation reactor, the volume of said liquid reaction medium being measured at ambient temperature. The water content of the crude acetic acid was approximately 4 to 7 wt %. This is to be compared with a water content of 20 to 25 wt % and an STY of 13 with the same rhodium concentration where, in accordance with the usual practice of the prior art, the carbonylation reactor was operated with a water content of approximately 15 wt % in the reaction medium.

As indicated by periodic analyses of the contents of the carbonylation reactor, there was very little precipitation of catalyst from the reaction medium in the flasher column and in the transfer lines recycling the catalyst solution from this column back to the carbonylation reactor, although our experience with solutions without iodide salts as in the prior art would have led one to predict a serious catalyst-loss problem.

When using other iodide salts, the controlling factor is the concentration of iodide moiety supplied by whatever salt is employed. That is, the beneficial results obtained with a given concentration of lithium iodide will also be obtained with other iodide salts when they are used in a concentration such that the molar equivalent iodide concentration is the same as that obtaining with a given lithium iodide concentration known to be effective.

An unexpected effect of operating the reaction system by the low-water method just described is also that there is a great reduction (by an order of magnitude) in the rate of formation of by-product propionic acid, the presence of which in the product acetic acid is objectionable for several reasons. Again as compared with the relatively high-water operating conditions of the prior art, there is a substantial reduction in the rate of formation of hydrogen and carbon dioxide, which, of course, are undesirable reaction products. These are formed by the water-gas shift reaction from carbon monoxide and water. The following tabulation compares yields of propionic acid (HOPr), carbon dioxide, and hydrogen obtained at the above conditions of 4 to 5 wt % water with those obtained using 14 to 15 wt % water in the reaction system characteristic of the prior art (no iodide salt). Methyl acetate content of the reaction medium was about 1 wt % in the high water medium and about 4 wt % in the low water system.

TABLE III

| Reactor H$_2$O | CO$_2$ Make (Moles CO$_2$/100 moles HOAc) | H$_2$ Make (Moles H$_2$/100 moles HOAc) | HOPr (ppm) | Acetic Acid % Yield Based on MEOH |
|---|---|---|---|---|
| 4–15% (No iodide salt) | 2.3 | 1.9 | 1435 (1) | 99 (2) |
| 4–5% (Iodide salt as described above) | 0.2 | 0.1 | 91 (1) | 99 (2) |

(1) In acid product from base of MeI-HOAc splitter.
(2) Approximate, within experimental margin of error. As calculated, yield was slightly higher in the "low water" case.

EXAMPLE 2

Other iodide salts are as efficacious as lithium iodide at the same iodide moiety concentration in the reaction medium. For example, in the continuous reaction system described in Example 1 a run was made in which the iodide salt was sodium iodide. Operating in the same manner as described with lithium iodide in Example 1, but with the iodide concentration being reduced because of the limited solubility of sodium iodide as compared with lithium iodide, the run was made under conditions as set forth in Table IV below. The reaction medium was as tabulated below, with acetic acid making up the balance in each tabulated case.

The results as tabulated show that, at the same concentration of iodide moiety, sodium iodide gave results as good as those obtained with lithium iodide. Specifically, within the indicated limits of accuracy, results were identical. When using the higher water concentration characteristic of the prior art but with no iodide salt, the acetic acid spacetime yield was slightly higher, but it is to be kept in mind that this was at the expense of having to work in the recovery system with a crude reaction medium containing 14 wt % water instead of 4 wt %. It is also to be kept in mind that in actual application of the present invention the iodide concentration would have preferably been higher than the indicated 9.4 wt %, which was the maximum concentration which could be used in the present Example in order to maintain comparability with sodium iodide, the solubility characteristics of which precluded using the higher concentrations which would actually be preferred.

TABLE IV

| Promoter/Stabilizer Iodide Salt | NaI | LiI |
|---|---|---|
| Inorganic Iodide (wt %) | 9.5 | 9.4 |
| Temperature (°C.) | 190 | 190 |
| Water, (wt %) | 4.0 | 4.0 |
| Methyl Iodide (wt %) | 12.2 | 12.1 |
| Methyl Acetate (wt %) | 3.1 | 3.1 |
| Rhodium (ppm) | 400 | 400 |
| Acetic Acid STY (mol/l · hr) | 14.3 | 12.7 |
| Carbon Dioxide STY (mol/l · hr) | 0.39 | 0.35 |
| Propionic Make Rate (lb/MM lb acetic acid) | 150 | 109 |
| Rhodium Loss, (ppm/hr) | 0.75 | 0.73 |

Figure 9:
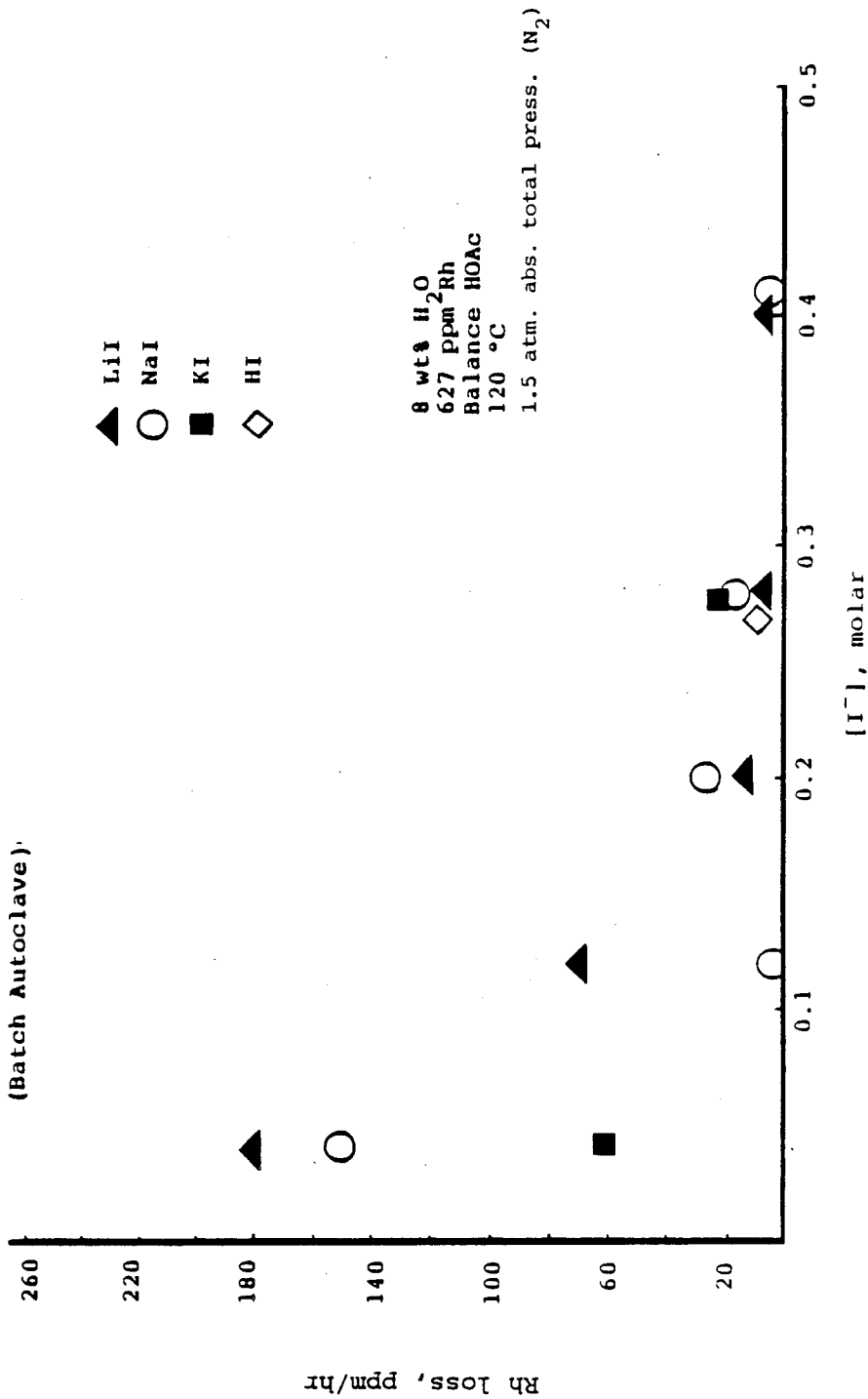

The effect of using a variety of iodide salts is set forth in Table V below. These data are all from runs which were carried out in the batch autoclave operated in the manner previously described. These data indicate that other iodide salts have a rate acceleration (promoting) action as well as does lithium iodide. FIG. 9 shows stabilizing action of several specific iodides. However, many of these do not have a very high solubility when the reaction medium is cooled much below normal operating temperature. Lithium iodide continues to be preferred because of its superior solubility characteristics.

TABLE V

Rate of Methanol Carbonylation With Various Iodide Sources
Batch Autoclave
Charge: 19 wt % MeI, 472 ppm Rh, 27 wt % MeOAc,
0.75 M I$^-$(equiv. to 10 wt % LiI)
28.2 atm. abs., 190° C.

| Salt | 2 wt % H$_2$O STY | 4–5 wt % H$_2$O STY | Comments |
|---|---|---|---|
| no salt | 3.0 | 10.9 | |
| LiI | 12.2 | 14.8 | Soluble |
| NaI | 8.8 | — | soluble |
| KI | 11.2 | 13.2 | partially soluble |
| RbI | — | 4.3 | poor solubility |
| CsI | — | — | insoluble |
| MgI$_2$ | 10.7 | 12.7 | partially soluble |
| CaI$_2$ | 17.2 | — | soluble |
| SrI$_2$ | 7.0 | — | soluble |
| BaI$_2$ | 11.2 | 15.9 | soluble |
| CoI$_2$ | 12.6 | — | soluble |
| SbI$_3$ | — | — | insoluble |
| ZnI$_2$ | 5.1 | 11.5 | soluble |
| SnI$_2$ | 1.3 | — | soluble |
| FeI$_2$ | 3.8 | 13.5 | partially soluble |
| LaI$_3$ | — | 16.7 | partially soluble |
| NiI$_2$ | — | 3.5 | insoluble |
| MnI$_2$ | 8.9 | — | soluble |
| NMPI | 10.1 | — | soluble |
| (Ph) (CH$_3$)$_3$H$^+$I$^-$ | 6.1 | — | partially soluble |
| Bu$_4$H$^+$I$^-$ | 7.1 | — | soluble |
| (Et) (Ph)$_3$P$^+$I$^-$ | 8.9 | — | soluble |

TABLE V-continued

Rate of Methanol Carbonylation With Various Iodide Sources
Batch Autoclave
Charge: 19 wt % MeI, 472 ppm Rh, 27 wt % MeOAc,
0.75 M I⁻ (equiv. to 10 wt % LiI)
28.2 atm. abs., 190° C.

| Salt | 2 wt % $H_2O$ STY | 4-5 wt % $H_2O$ STY | Comments |
|---|---|---|---|
| $NH_4{}^+I^-$ | 4.67 | — | insoluble |

It will be understood that the foregoing Examples are given merely by way of illustration and that many departures can be made therefrom within the scope of the invention. In particular it will be understood that the heart of the invention lies in controlling the carbonylation reactor itself so as to produce a product mixture having a low water content as compared with the prior art while avoiding losses in reactor productivity. The product-recovery system exemplified above is one which, while industrially applicable, was especially selected for ease of control while studying and demonstrating the invention. It will be obvious to those skilled in distillation that, to divide the drawn-off carbonylation reaction medium into a recycle catalyst stream, a crude acetic acid product stream, and a recycle or recycles comprising methyl iodide and methyl acetate, many alternatives are easily foreseeable among which the process designer can select what he views as the optimum for reliable and economical operation in his own circumstances.

The drawings FIGS. 1-25 describe the interaction of the several process parameters the manipulations of which is important in the practice of the present invention. Some of these figures set forth the results of runs carried out in the batch autoclave (operation previously described herein), some present the results of runs carried out in the continuous pilot plant unit (operation also described previously herein), and some are based on results obtained in a batch-operated glass vessel which was designed specifically to study catalyst stability. This vessel was actually composed of two side-by-side vessels fabricated from glass pipe and designed to operate at pressures not to exceed about 2 atmospheres gauge pressure at 150° C. To conduct a run, each of the glass vessels was initially charged with the desired weight of rhodium (as salts like $RhI_3$), HI, acetic acid, water, and stabilizer. Both vessels were then pressurized to about 1.8 atmospheres gauge with carbon monoxide and heated in an oil bath to 130° C. or 150° C. in order to dissolve the rhodium. Carbon monoxide was then bubbled into the solution at 47 ml per minute through a gas-inlet tube while the desired constant pressure was maintained by a back-pressure regulator system. After one hour, the carbon monoxide was replaced by nitrogen and the total pressure was reduced to about 1 atmosphere gauge. This was considered the initial time of the stability experiment. Samples were removed through a sampling port, centrifuged for 5-10 minutes, and the clear centrifugate analyzed for soluble rhodium content.

Turning now to the information set forth in the drawings and considering the drawings in numerical order:

FIGS. 1 through 9 show the results of batch experiments. FIG. 1 illustrates that reducing the water content of the reaction system does reduce the reaction space-time yield, but that with high lithium iodide in the reaction medium along with high methyl acetate and methyl iodide, good carbonylation rates can be obtained at surprisingly low water concentrations. It also shows the agreement of data obtained in batch autoclave and the continuous unit.

Figure 2:
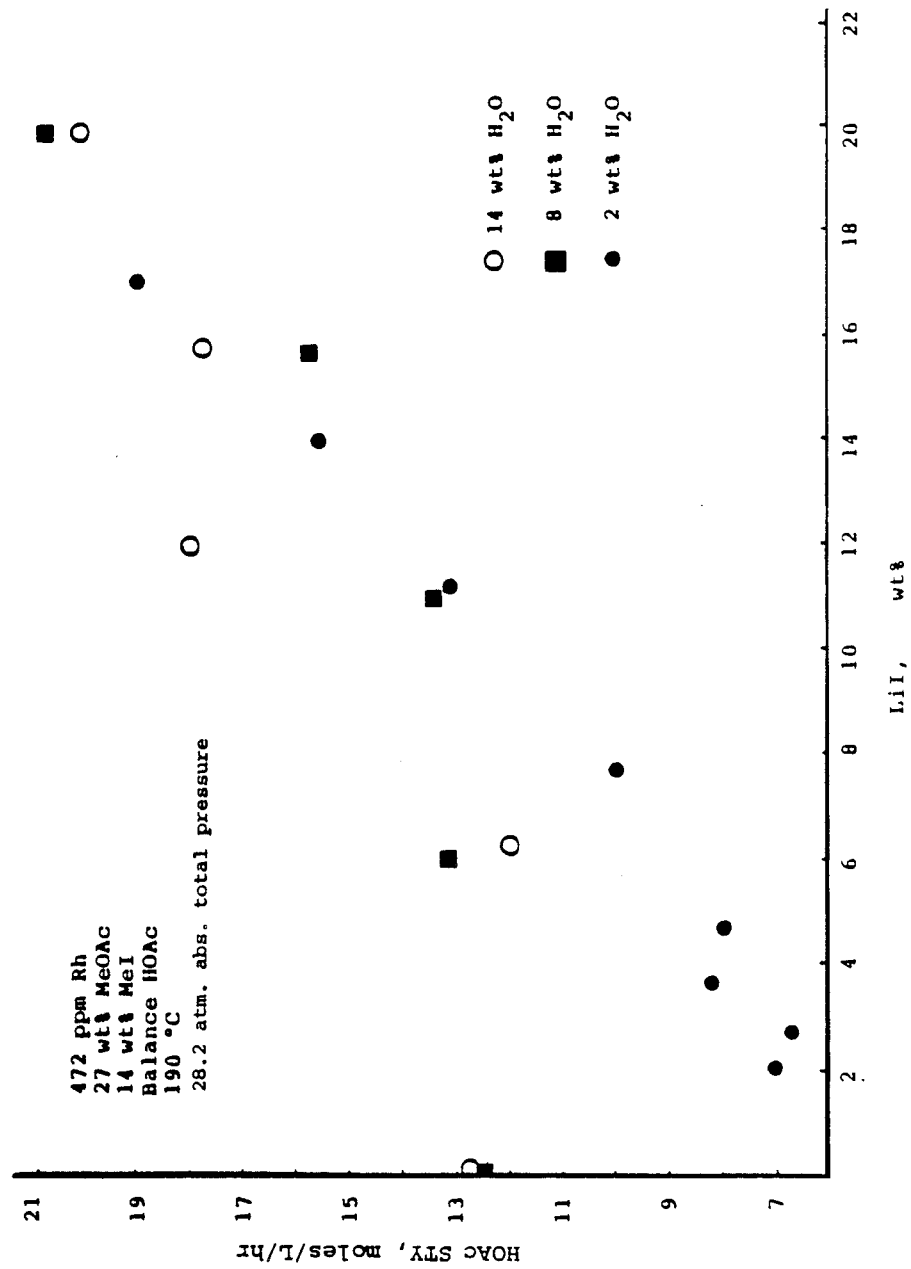

FIG. 2 illustrates that space-time yield increases with increasing lithium iodide concentration. Although there is some scatter in the data especially at high water concentration, it is also indicated that increasing the lithium iodide concentration mitigates what would otherwise be the adverse effect on reaction rate of reducing the water concentration. The effect of iodide at low water (2 wt %) is very well defined and impressive.

Figure 3:
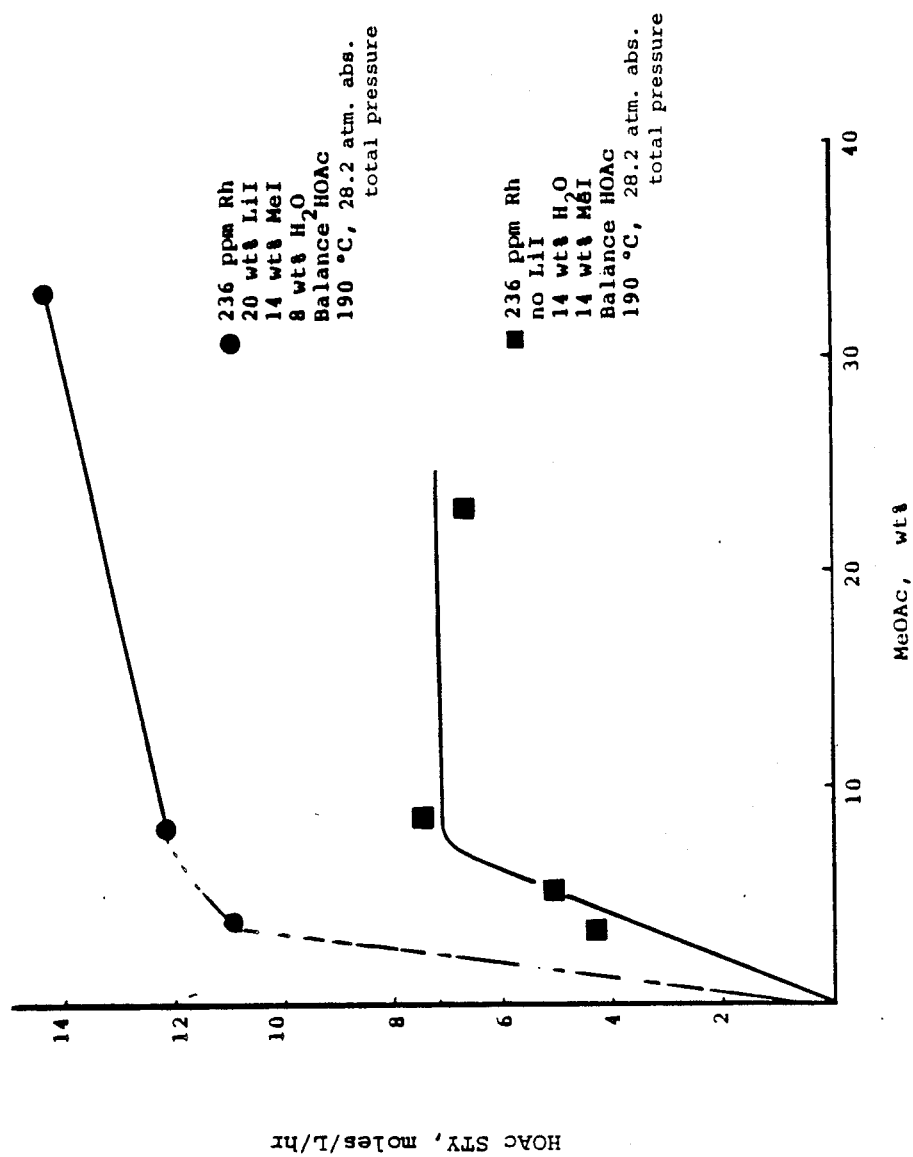

FIG. 3 demonstrates that the methyl acetate concentration is a significant factor and that it is inter-related with the employment of the lithium iodide stablizer. Both with and without lithium iodide being present, increasing the methyl acetate concentration up to somewhat less than 10 wt % increases the space-time yield, but with 20% lithium iodide being in the reaction medium the space-time yield at a given methyl acetate concentration is roughly double that observed when the lithium iodide is not present even at lower water concentration.

Figure 4:
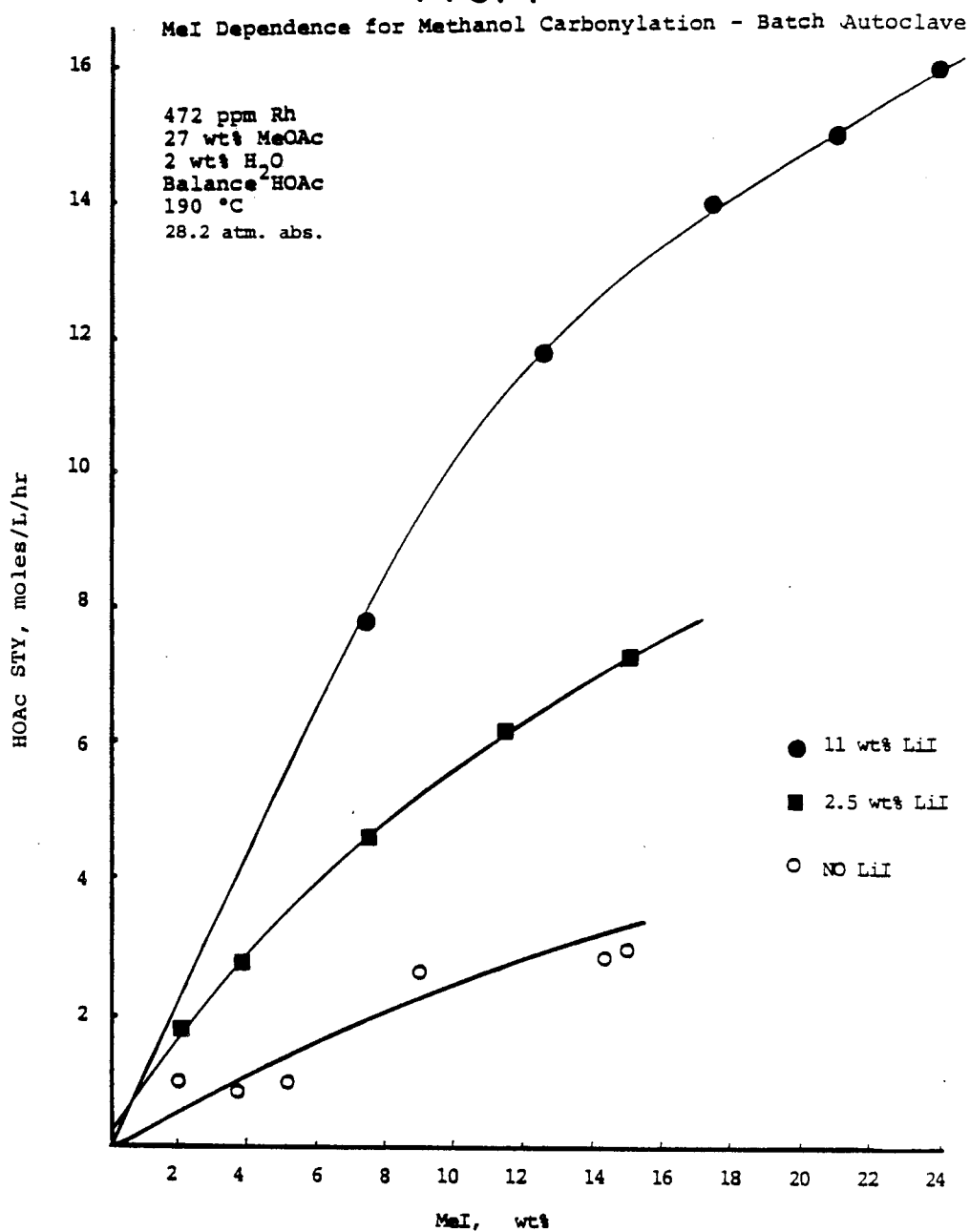

FIG. 4 illustrates the significance of methyl iodide concentration in the reaction medium with varying lithium iodide concentration. With no lithium iodide, space-time yield increases with increasing methyl iodide concentration but the space-time yields are relatively low. With 2.5 wt % lithium iodide in the mixture the space-time yields are higher than with none, still, however, showing a methyl iodide dependency. With 11 wt % lithium iodide the space-time yields are even higher, still showing an increase with increasing methyl iodide.

Figure 5:
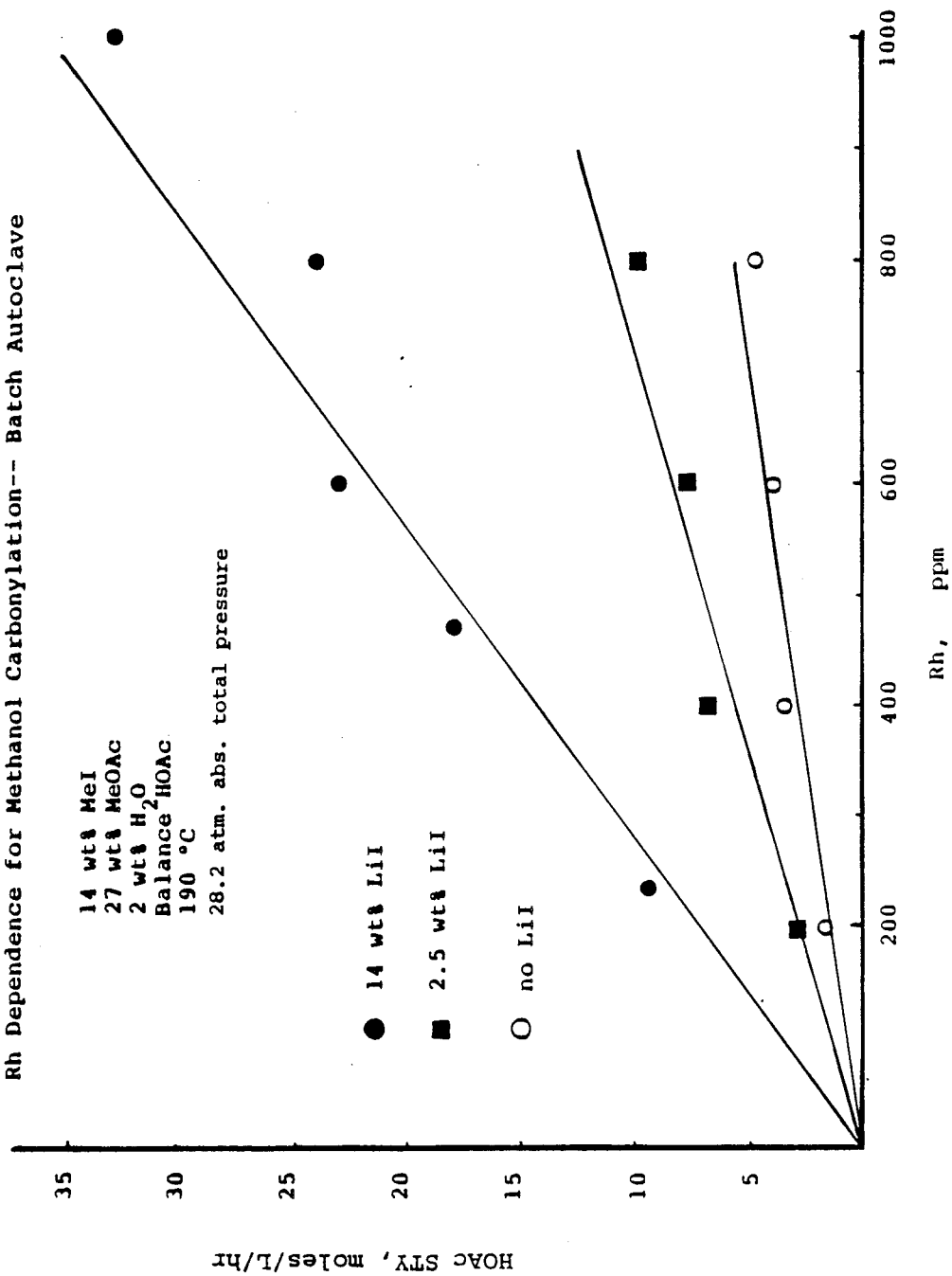

FIG. 5 demonstrates, not surprisingly, that the space-time yield increases with increasing rhodium concentration in the reaction medium. It is further demonstrated, however, that results are poorest when there is no lithium iodide present, better when there is 2.5 wt % lithium iodide, and (within the range illustrated here) best when the lithium iodide concentration is 14 wt %.

Figure 6:
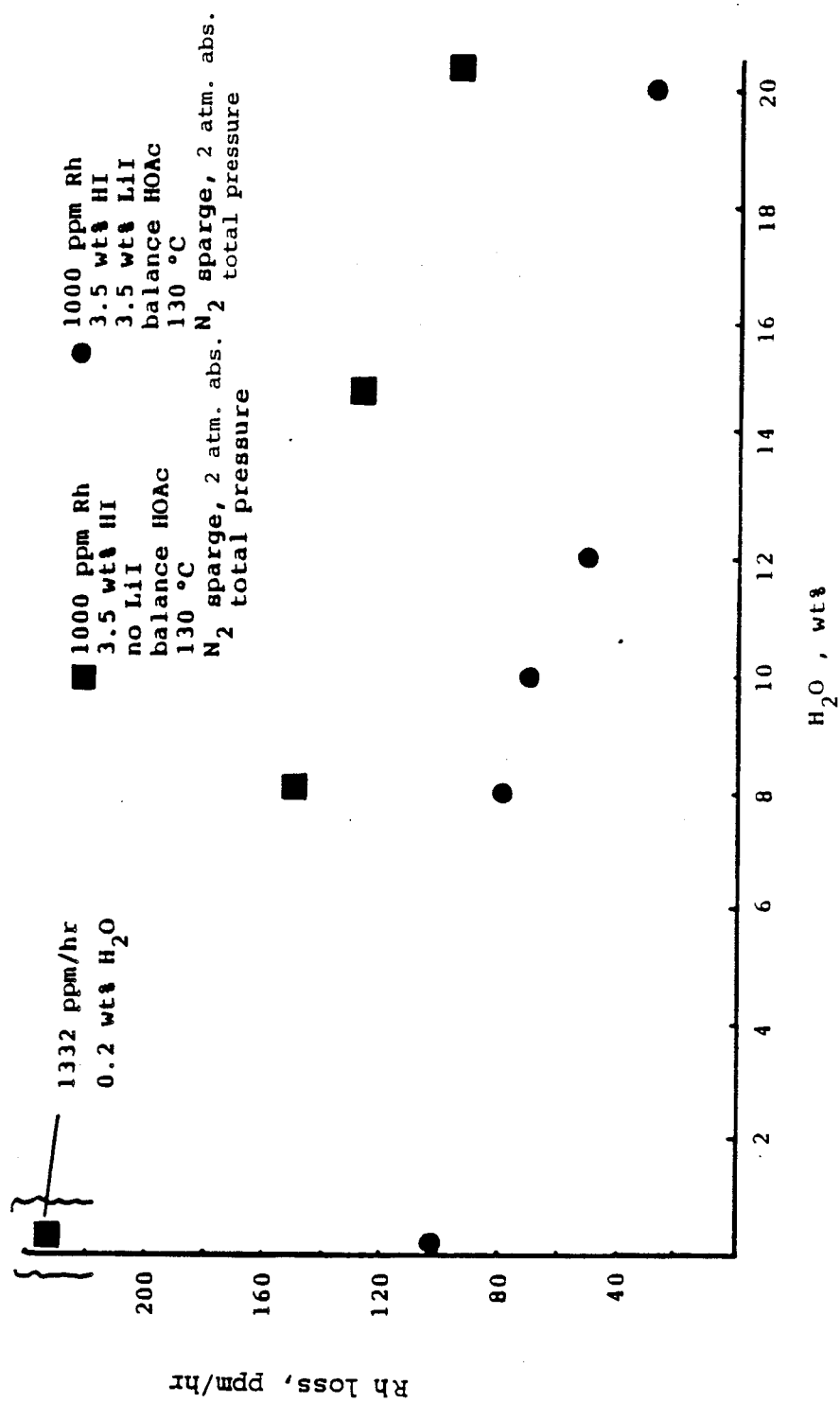

FIG. 6 illustrates that increasing water in the reaction medium decreases the rate of rhodium catalyst precipitation. Also illustrated in FIG. 6, an increase in iodide moiety by adding lithium iodide reduces the rate of rhodium precipitation out of the reaction medium at a given hydrogen iodide and water concentration.

Figure 7:
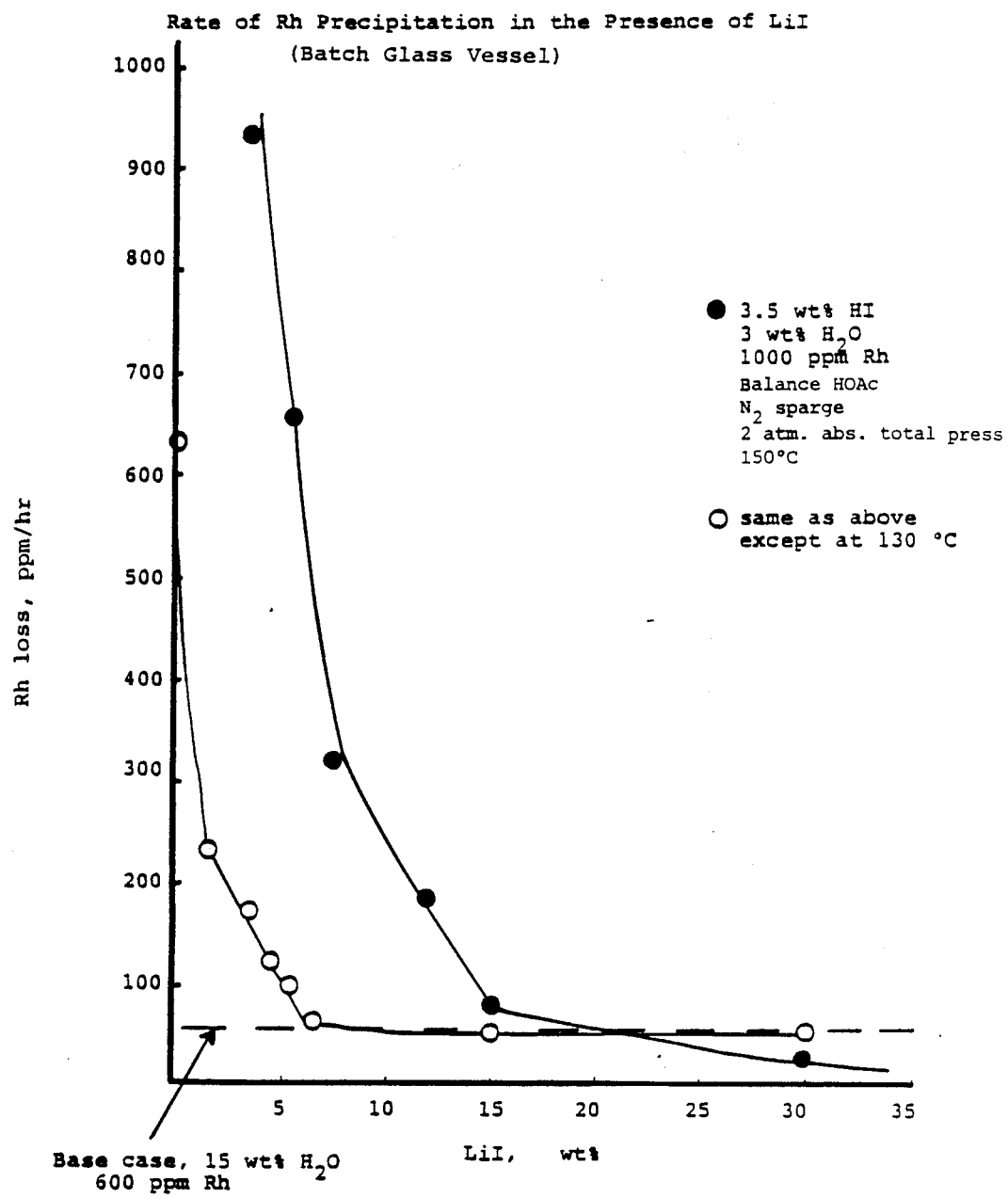

FIG. 7 illustrates the stabilizing effect of lithium iodide at low (3 wt %) water concentration and at two temperatures (130° C. and 150° C). At the lower temperature, roughly 6 wt % lithium iodide results in catalyst stability as good as that obtained when using a reaction medium containing 15 wt % water and needing no stablizer. At the higher temperature, about 15 wt % lithium iodide is adequate.

Figure 8:
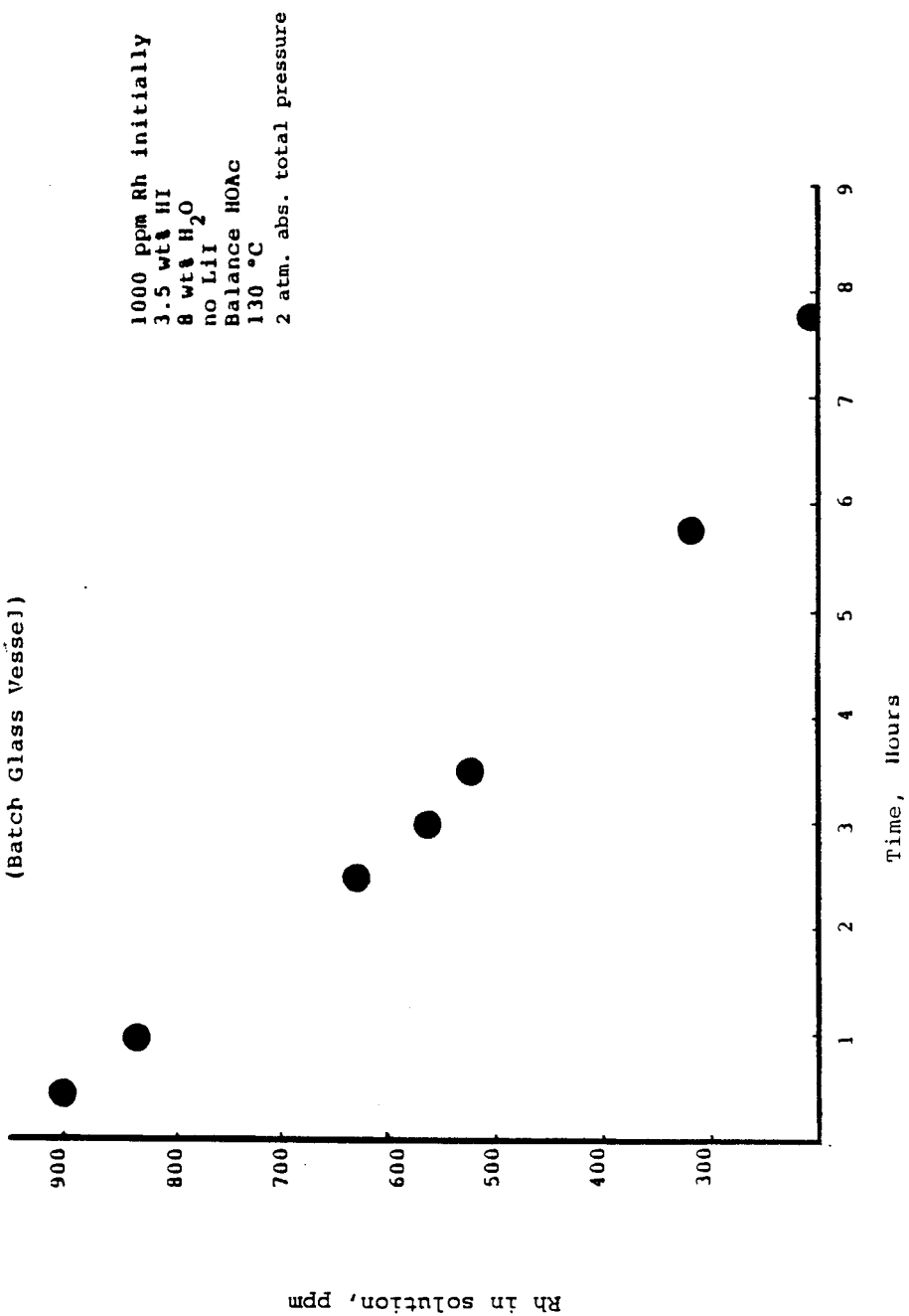

FIG. 8 it is demonstrated that, in the absence of lithium iodide, very little rhodium remains in solution after 8 hours or less in a reaction medium of the composition described.

FIG. 9, based on data obtained in the batch autoclave, illustrates that it is the halide (in this case iodide) moiety which is the significant factor in stabilizing the reaction catalyst. Note especially, for example, that at about 0.28 molar concentration of iodide the (low) rhodium loss per hour is essentially the same regardless of the source of the iodide.

Figure 10:
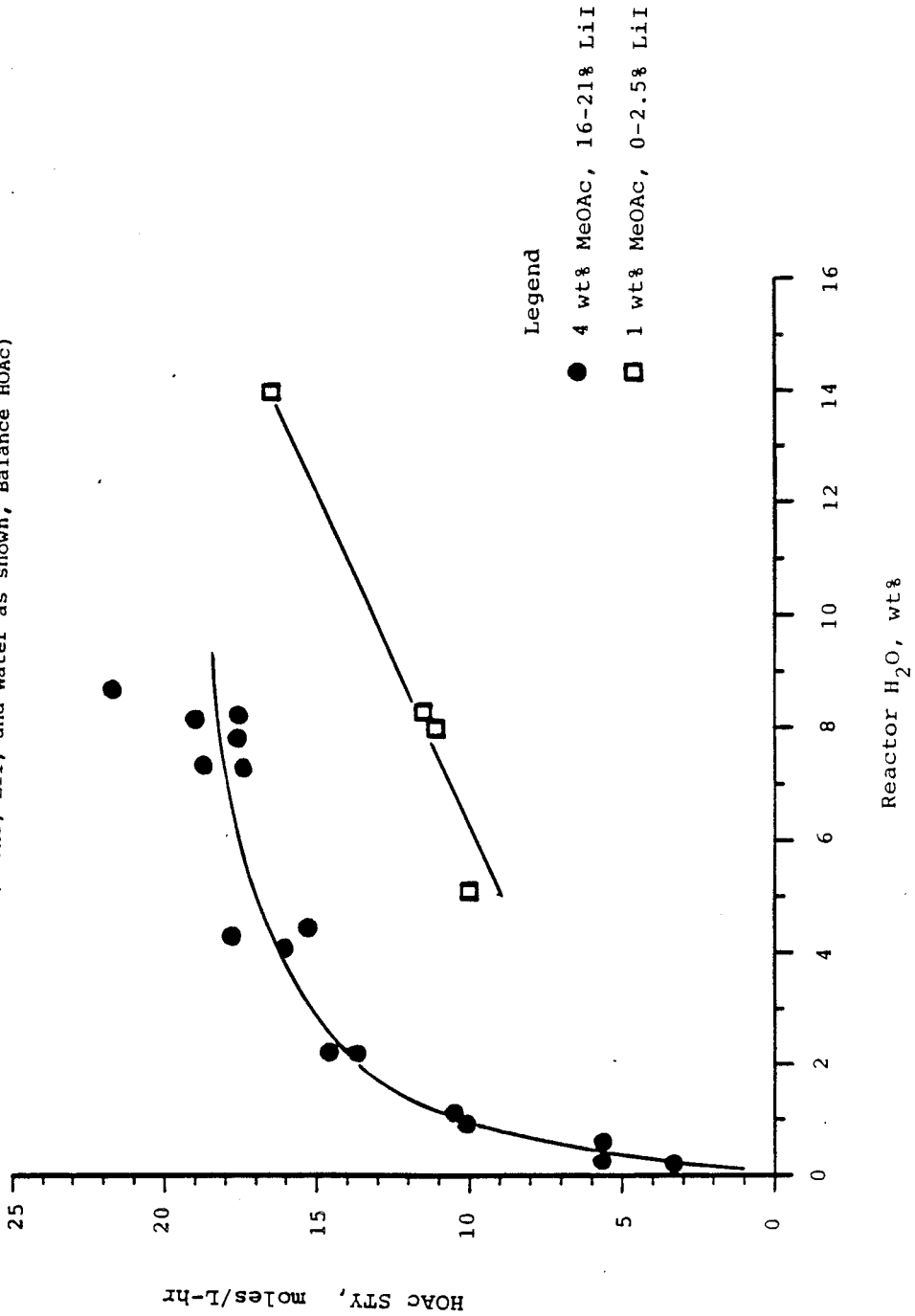

FIG. 10, as well as FIGS. 11-25, presents data taken from the continuous unit the operation of which has been previously described.

Figure 20:
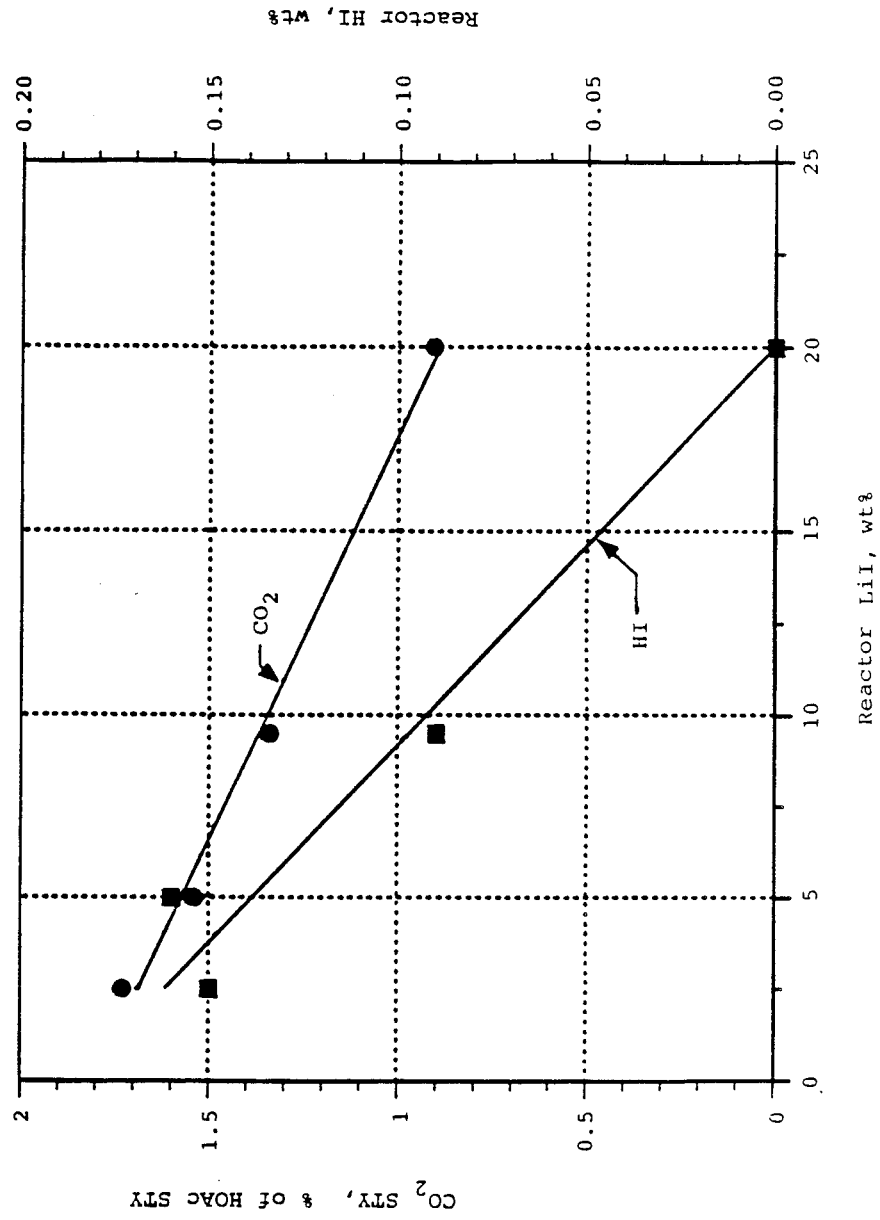
Figure 21:
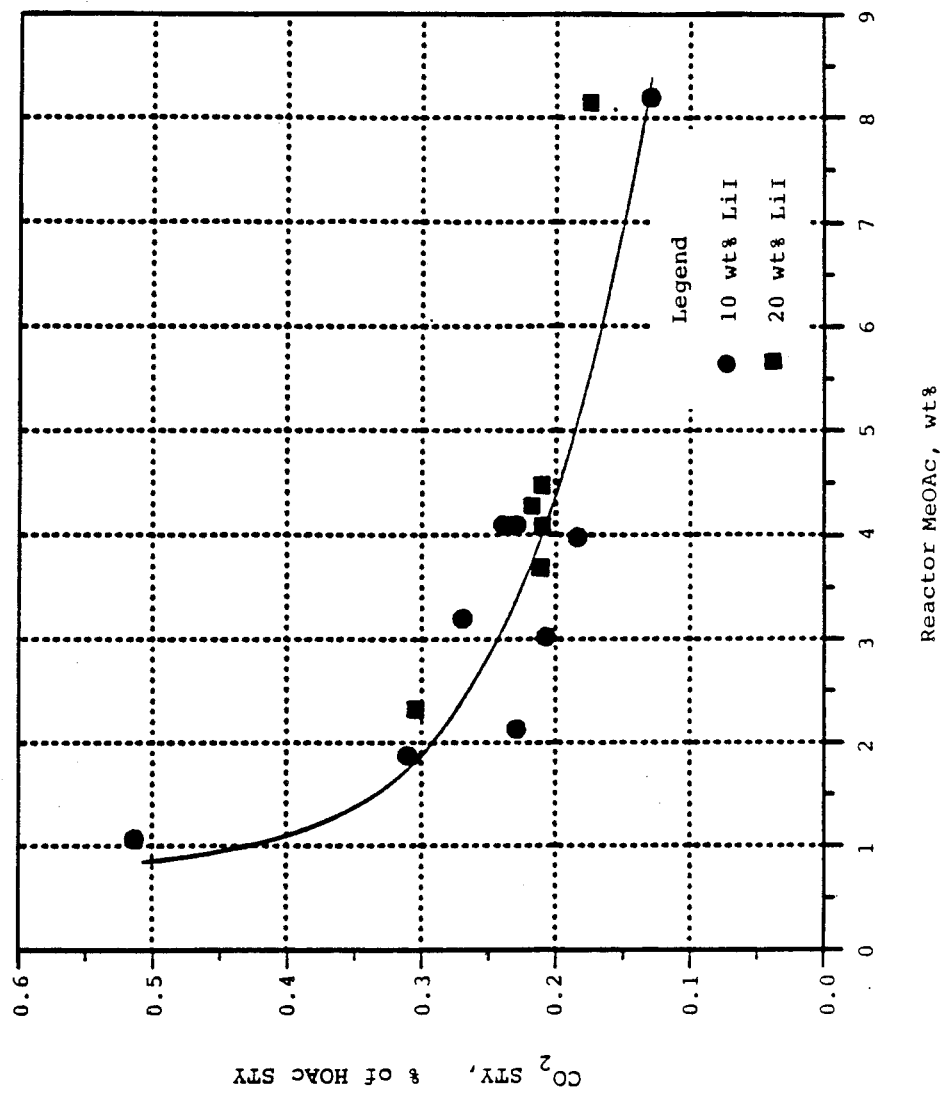
Figure 22:
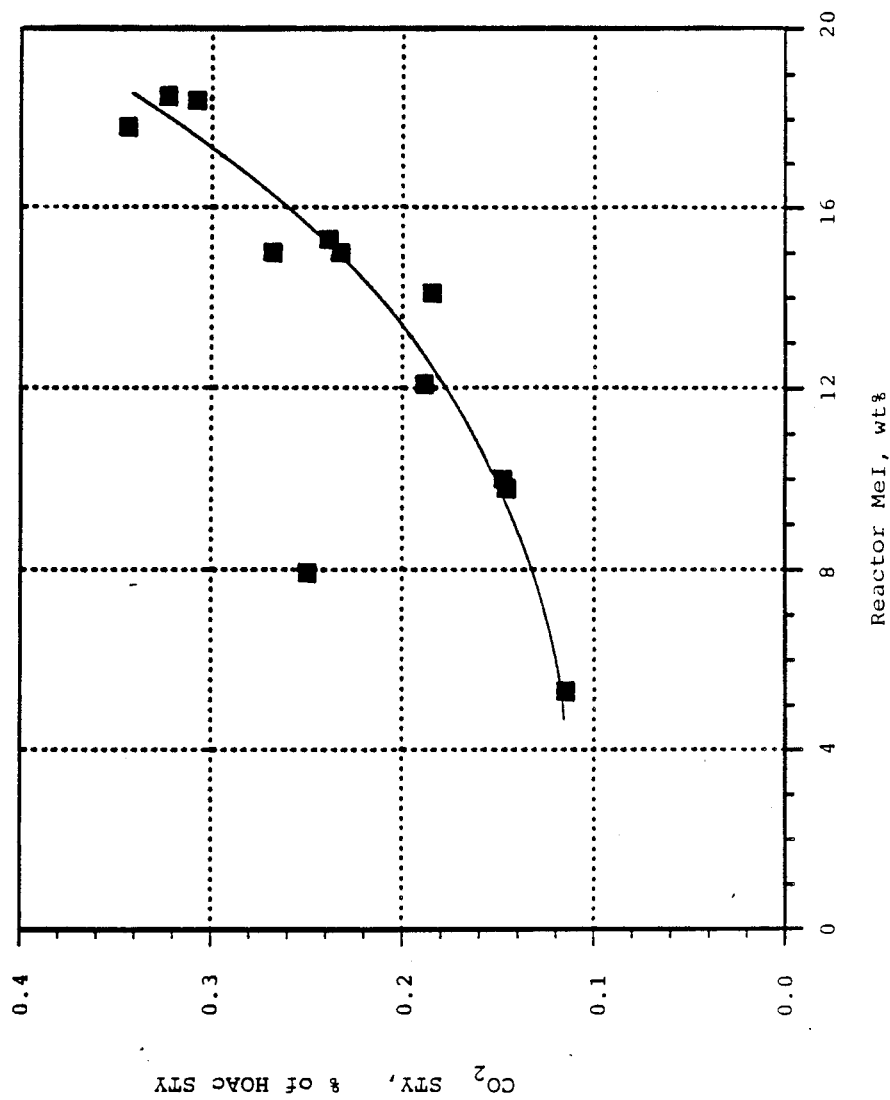

FIG. 10 itself illustrates that high lithium iodide together with high methyl acetate counteracts the deleterious effects on space-time yield of reducing the water concentration in the reaction medium. It will be seen that with 16 to 21 wt % lithium iodide and 4 wt % methyl acetate the space-time yields obtainable at 2 wt % water in the reaction medium are almost as good as those obtained at higher water concentrations of around, for example, 10 wt % with 1 wt % methyl acetate and 0-2.5 wt % lithium iodide. It should be explained, incidentally, that for data points at 4 wt % methyl acetate conditions set out in FIG. 10 there is a range of lithium iodide concentration. This is due to the fact that the steady state lithium iodide content is determined by an equilibrium between lithium iodide and lithium acetate which is affected by the change in reactor water and methyl acetate content. This will be shown later (FIG. 20). This is also true for similar figures to follow.

Figure 11:
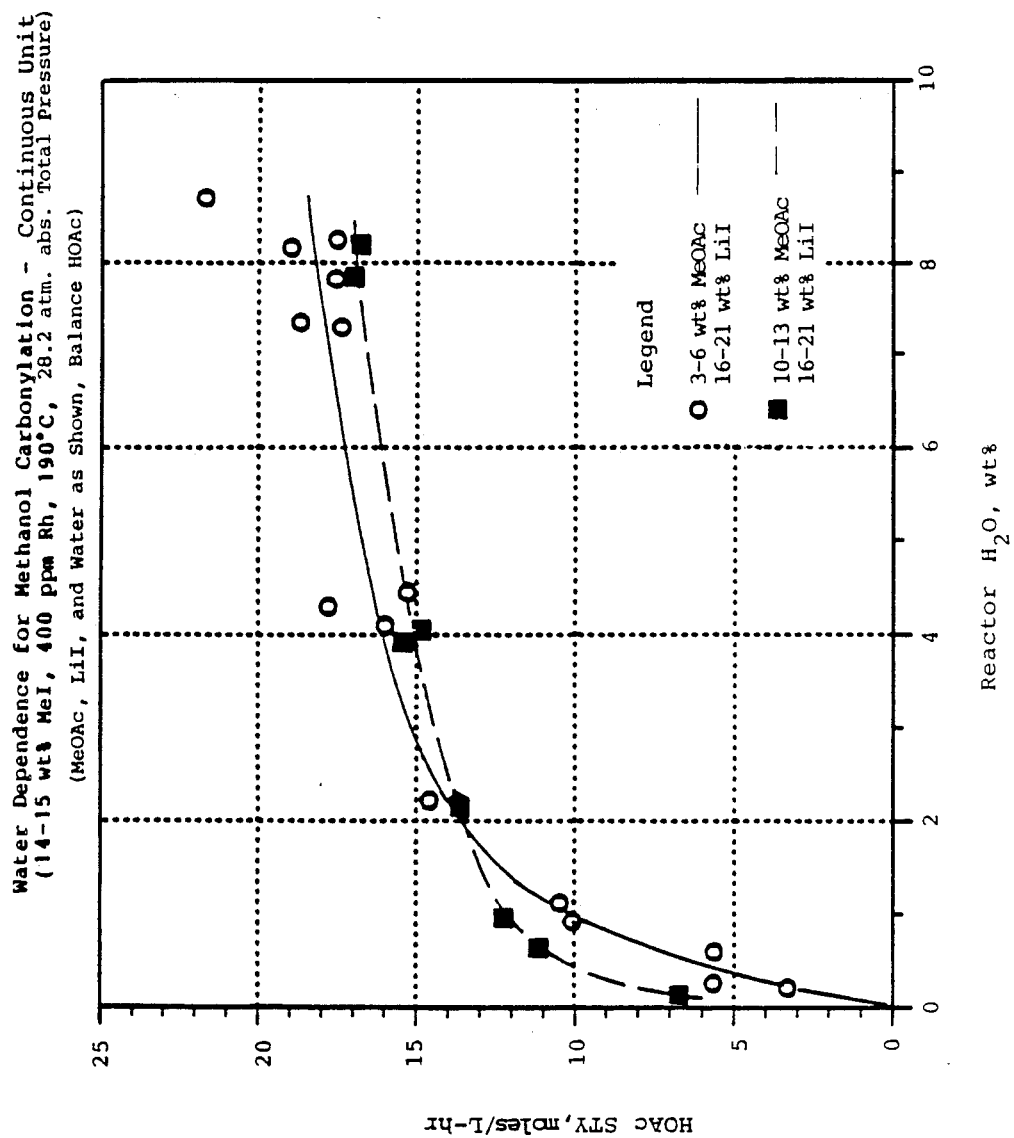

FIG. 11 illustrates that the reaction rate is dependent on water concentration even at high concentrations of lithium iodide, but that at about 1 wt % water the use of high lithium iodide brings the reaction rate up to about 10 to 12 moles per liter-hour and that above about 2 wt % water the use of high lithium iodide brings about space-time yields almost as high as those obtained at 8 wt % water and higher (FIG. 10).

Figure 12:
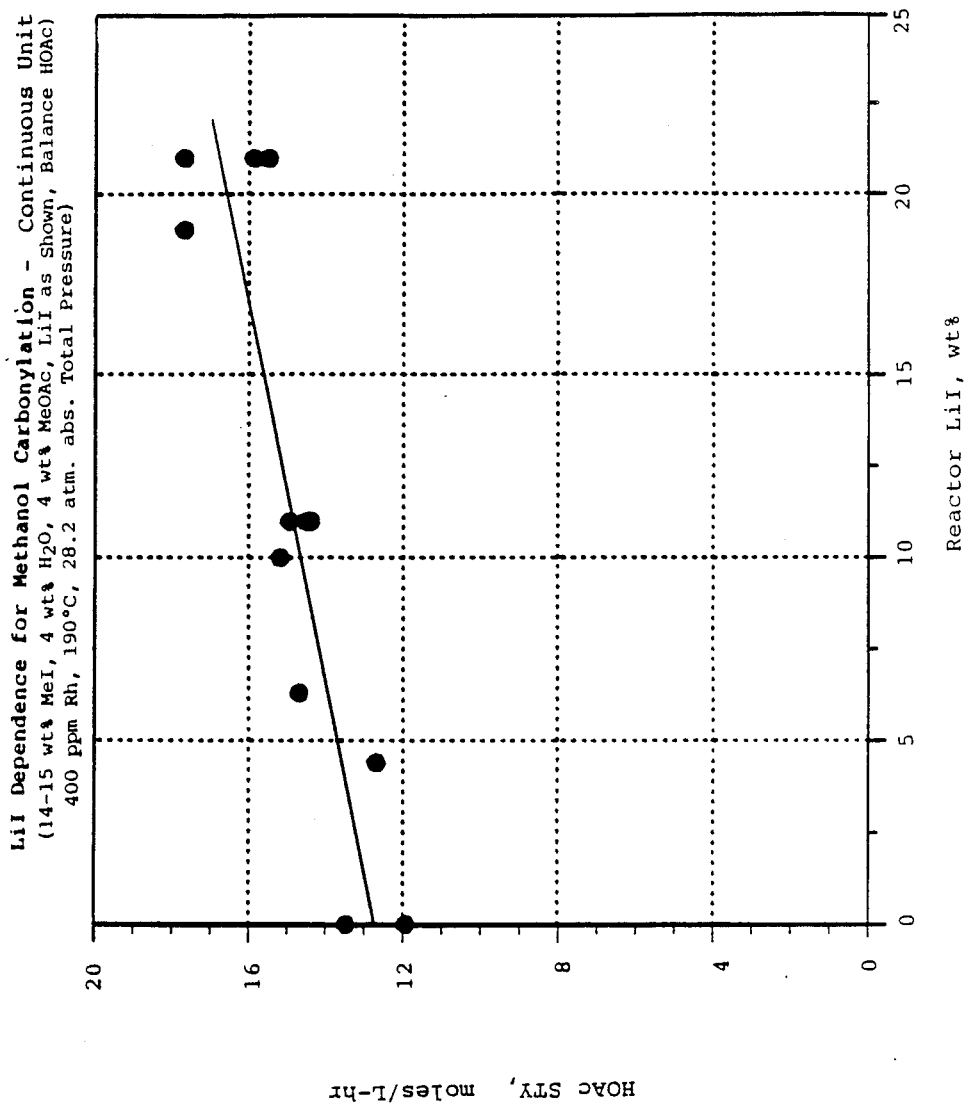
Figure 13:
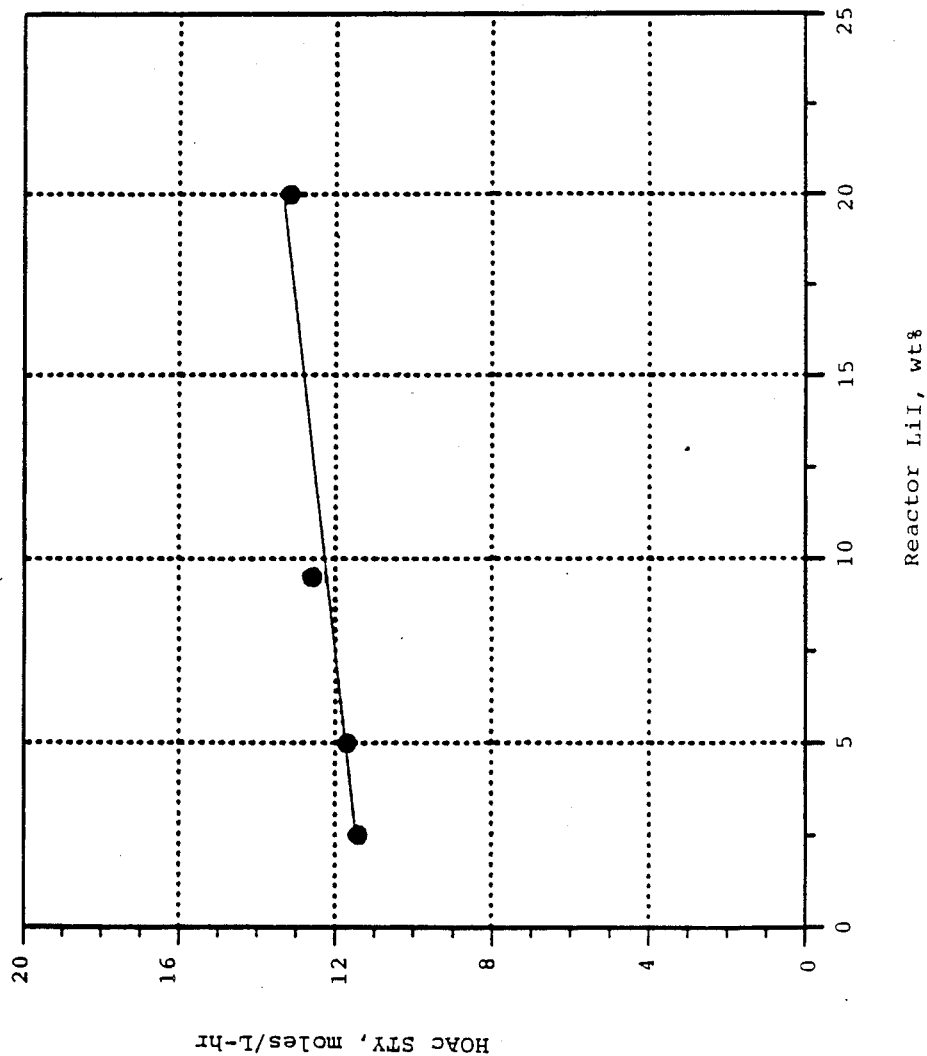

FIGS. 12 and 13 describe the effect of increasing lithium iodide concentration in increasing the space-time yield of acetic acid at two levels of methyl acetate in the reaction medium. These data, which are from the continuous unit, can be read in conjunction with FIG. 2, which presents data from the batch autoclave.

The effect of lithium iodide on the rate of methanol carbonylation under conditions of high water (8 wt %) and low methyl acetate (1 wt %) concentration as shown in FIG. 13 would appear to be relatively small in the range of 0-20 wt % lithium iodide (ca. 18% rate increase) when compared with FIG. 12 and also with FIG. 2 (batch). The differences are mainly due to the different methyl acetate and water concentrations used in the runs in the different figures. The higher the methyl acetate and the lower the water concentration the higher is the effect of lithium iodide on the rate. Because lithium iodide stabilizes the Rh catalyst, it becomes possible to decrease the reactor water concentration in order to increase throughput in the purification train. Also if the water concentration is decreased in conjunction with increasing the methyl acetate concentration, a significant rate enhancement due to lithium iodide is observed as shown in FIG. 12 (4 wt % water, 4 wt % methyl acetate, 0-21 wt % lithium iodide; 23-50% rate increase from 0-21 wt % lithium iodide) and in FIG. 2 (2-8 wt % water, 27 wt % methyl acetate and 2-20% lithium iodide, 200% rate increase from 2-20 wt % lithium iodide). Therefore, lithium iodide addition makes possible operation in a new concentration range of low water and high methyl acetate (FIG. 10), heretofore impossible because of low rates and severe catalyst instability. Further evidence for rate enhancement due to lithium iodide is given in FIG. 2 which shows that the lower the water concentration and the higher the methyl acetate concentration the greater the rate-enhancing effect of lithium iodide.

Figure 14:
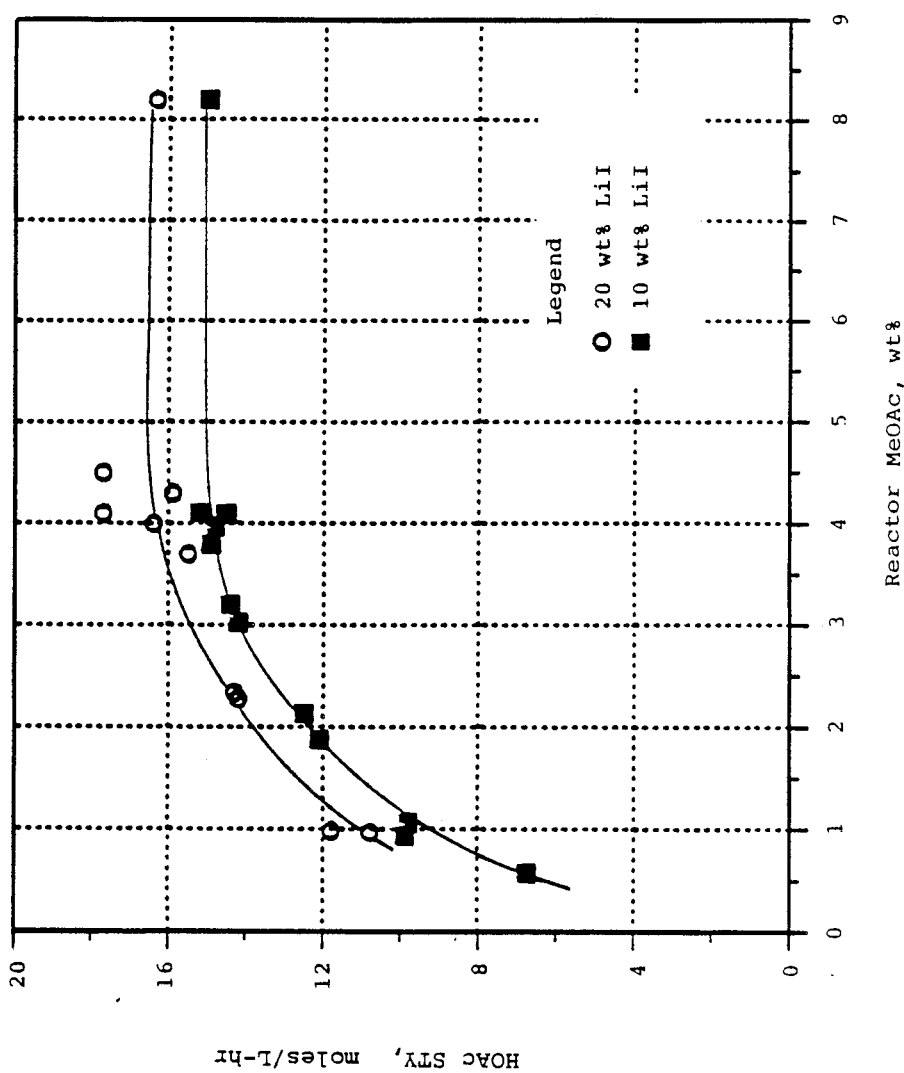
Figure 15:
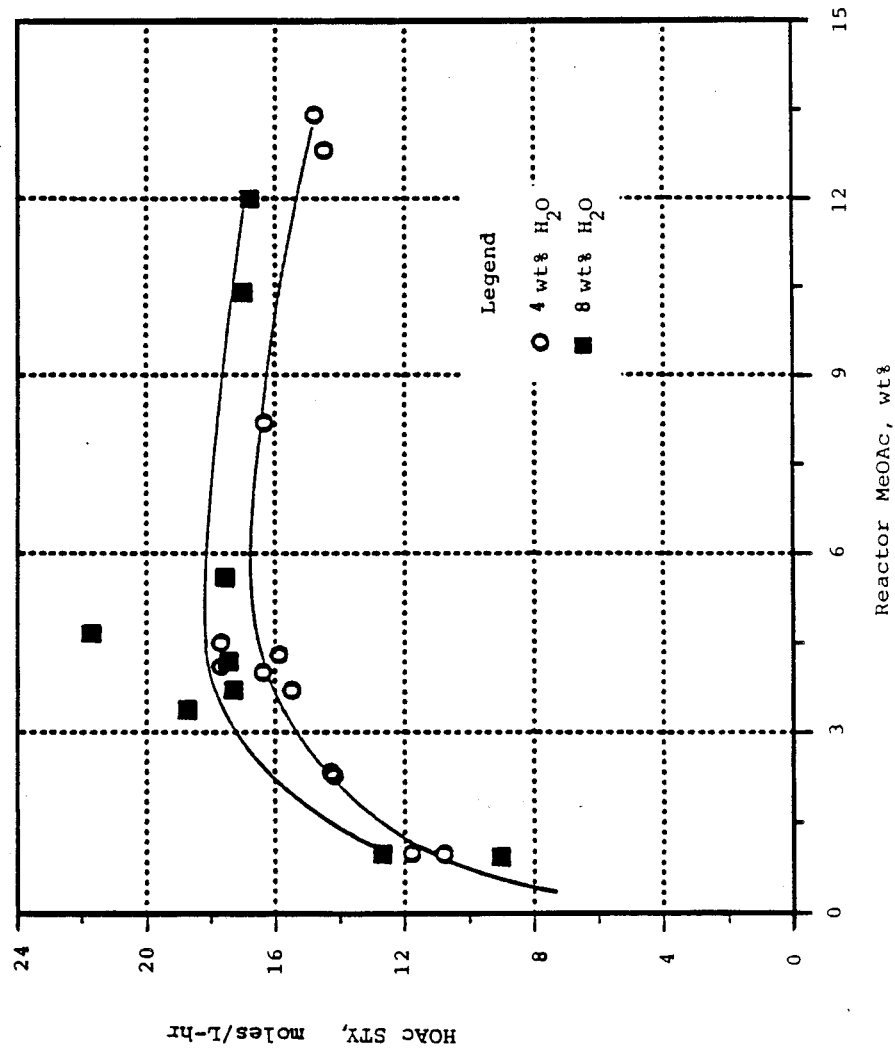

The effect of methyl acetate (in the presence of high lithium iodide concentrations) on the acetic acid space-time yield is shown in FIGS. 14 and 15. In both cases the effect of adding methyl acetate is beneficial up to a level of about 4 to 5 wt %, after which the effect levels off or (FIG. 15) declines slightly. Between 0 and about 3 wt %, the beneficial effect of adding methyl acetate is marked. Using 20 wt % lithium iodide is seen to be more beneficial than using 10 wt %, and space-time yield is somewhat better with 8 wt % water as compared with 4 wt %.

Figure 16:
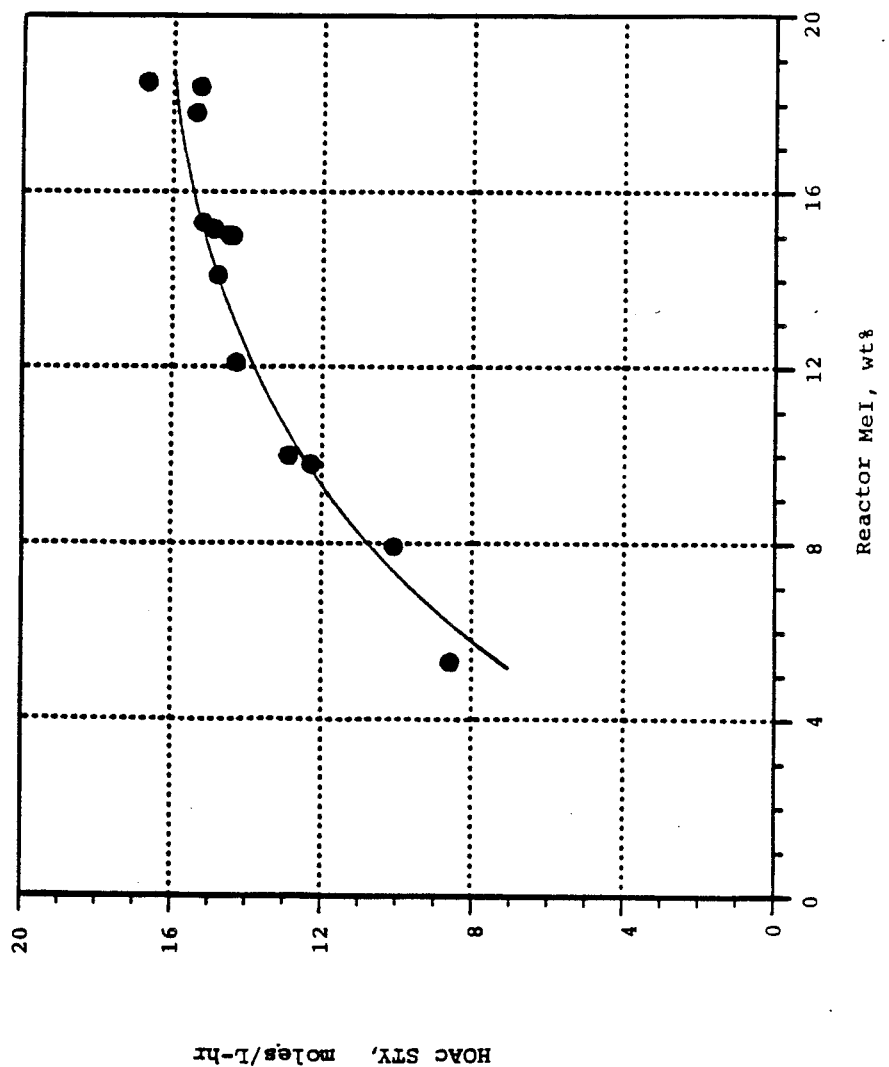
Figure 17:
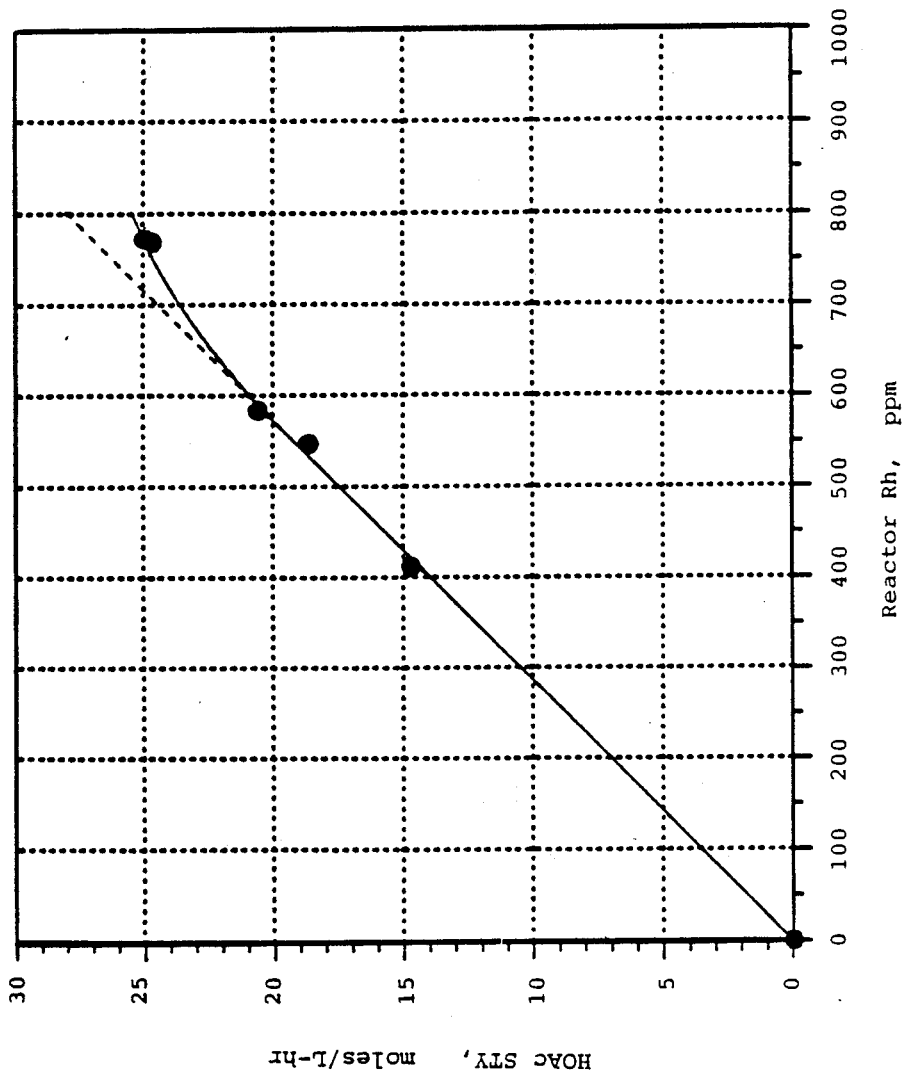

FIGS. 16 and 17 show that the acetic and space-time yield increases when increasing methyl iodide concentration and rhodium concentration respectively, as expected.

Figure 18:
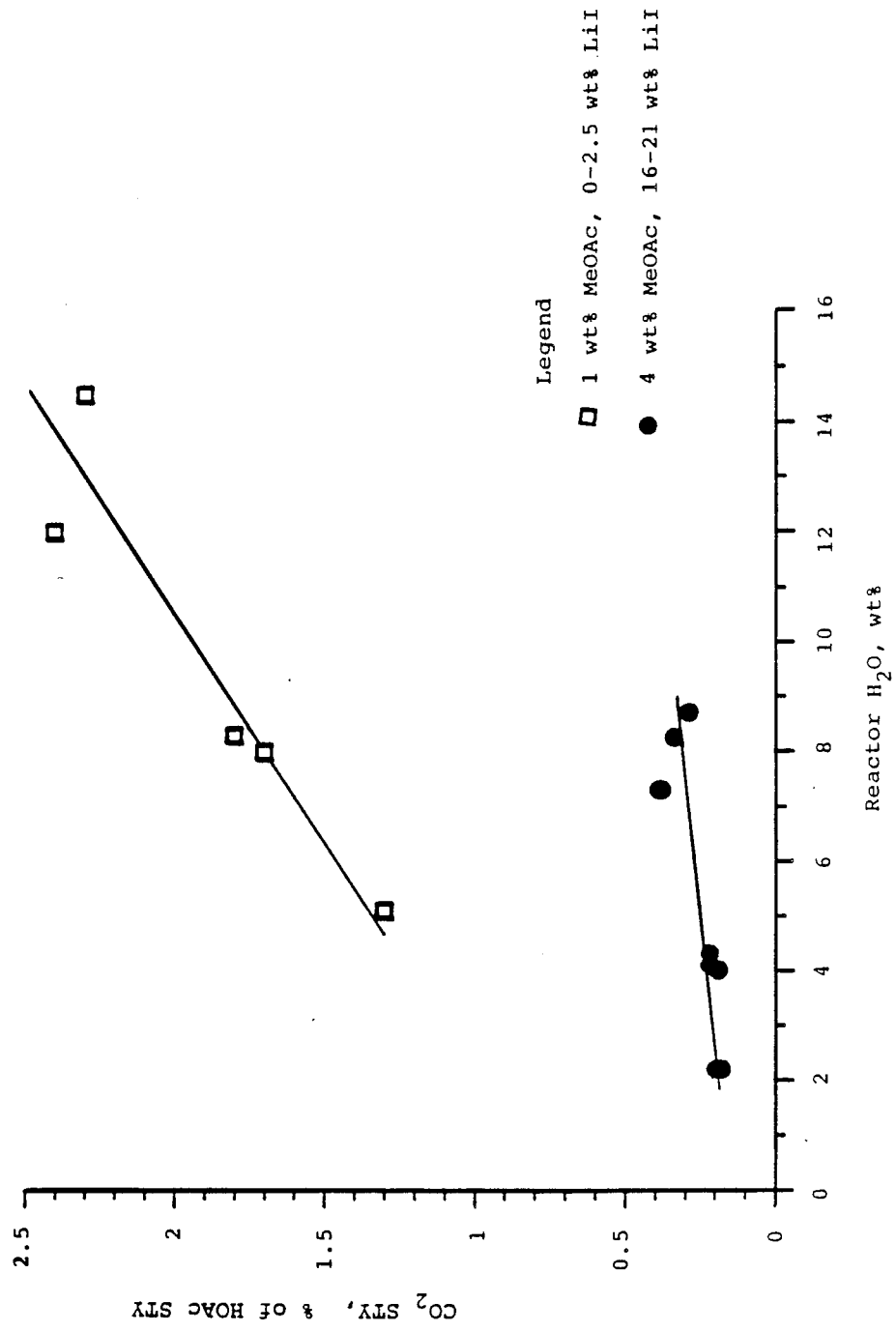
Figure 19:
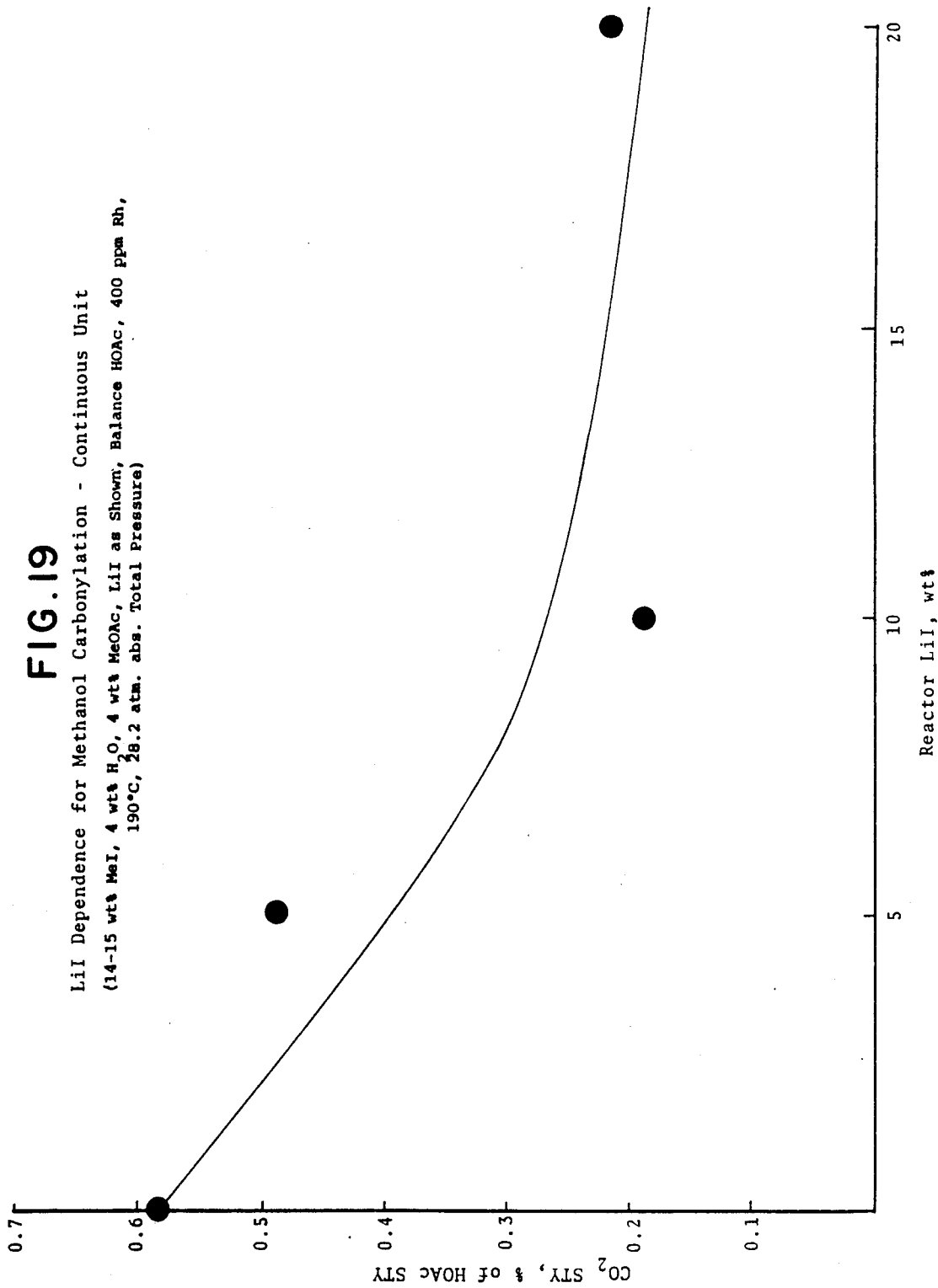

FIG. 18 illustrates the effect of lithium iodide, methyl acetate, and water on the (undesired) formation of carbon dioxide as a reaction by-product. When using 16 to 21 wt % lithium iodide and 4 wt % methyl acetate the generation of carbon dioxide is much lower than when using 0 to 2.5 wt % lithium iodide and only 1 wt % methyl acetate. It is also to be noted that reducing the water content with a given reaction medium has the effect of reducing the rate of formation of carbon dioxide. Reducing carbon dioxide formation in this manner, by using the lithium iodide or equivalent stabilizers of the present invention, is another unexpected result of operating in the low-water reaction medium the use of which is made possible by employing these stabilizers. FIGS. 19, 20, 21, and 22 further show the individual effects of lithium iodide, methyl acetate, and methyl iodide at low water concentration (4 to 8 wt %) on the formation of carbon dioxide. FIG. 20 also shows the equilibrium concentration of hydrogen iodide at various lithium iodide concentrations.

Figure 23:
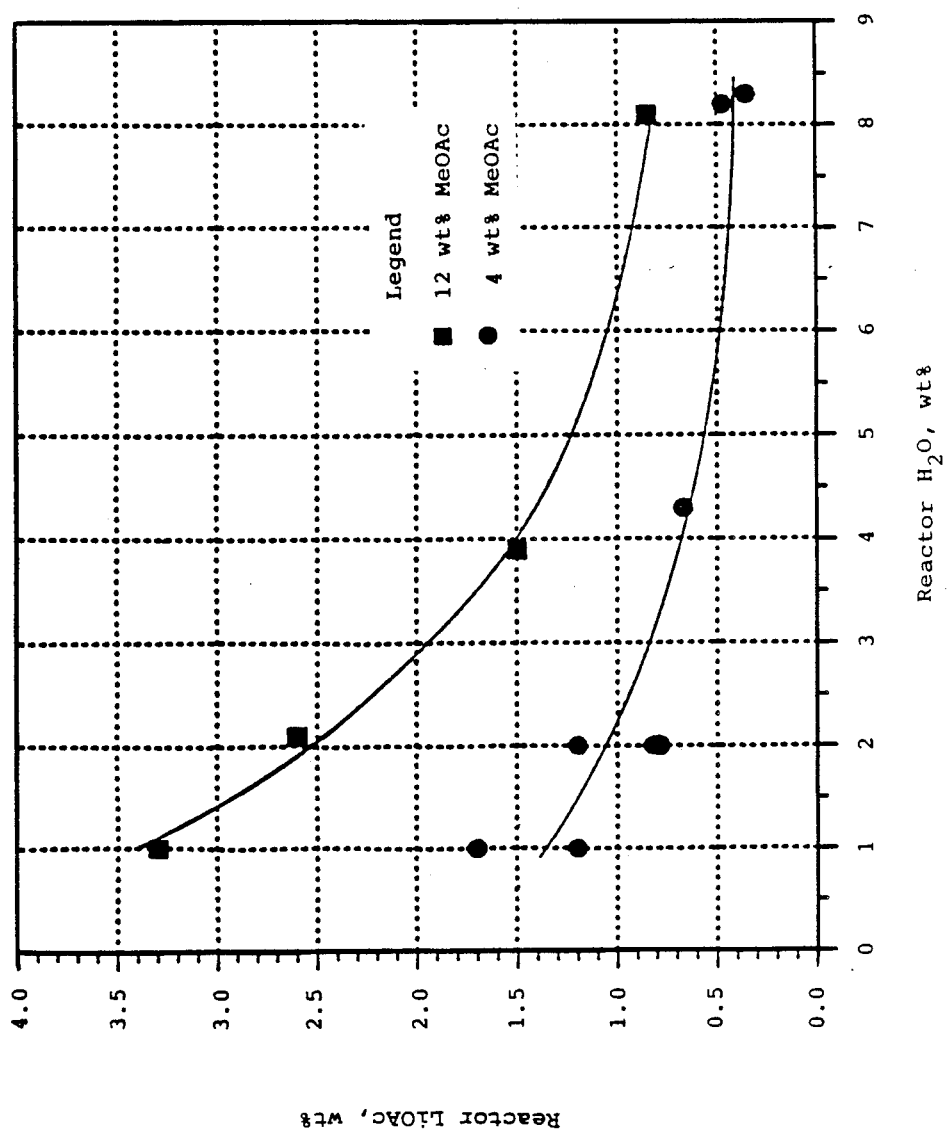

FIG. 23 deals with the equilibrium existing in the reaction medium between lithium iodide and lithium acetate:

$$LiI + MeOAc \rightleftharpoons LiOAc + MeI$$

with decreasing water content the lithium acetate content of the reaction medium increases, this effect being greater when 12 wt % methyl acetate is present as compared with 4 wt %. This equilibration between lithium iodide and lithium acetate which is dependent on the water concentration of the reaction medium has been found, incidentally, to have no adverse effect on the behavior of the catalyst system. As a matter of fact this equilibrium will allow the increasing of the lithium iodide concentration of the reaction medium by adding, if desired, lithium acetate or other lithium salts. Because of this equilibrium one cannot distinguish the effect of lithium iodide from that of lithium acetate on the reaction rate and it is possible that both the lithium iodide and lithium acetate increase the reaction rate, especially with catalyst solutions with low water concentration. However, the important fact is that adding either lithium acetate or lithium iodide one obtains eventually the same equilibrium mixture of both salts in solution.

Figure 24:
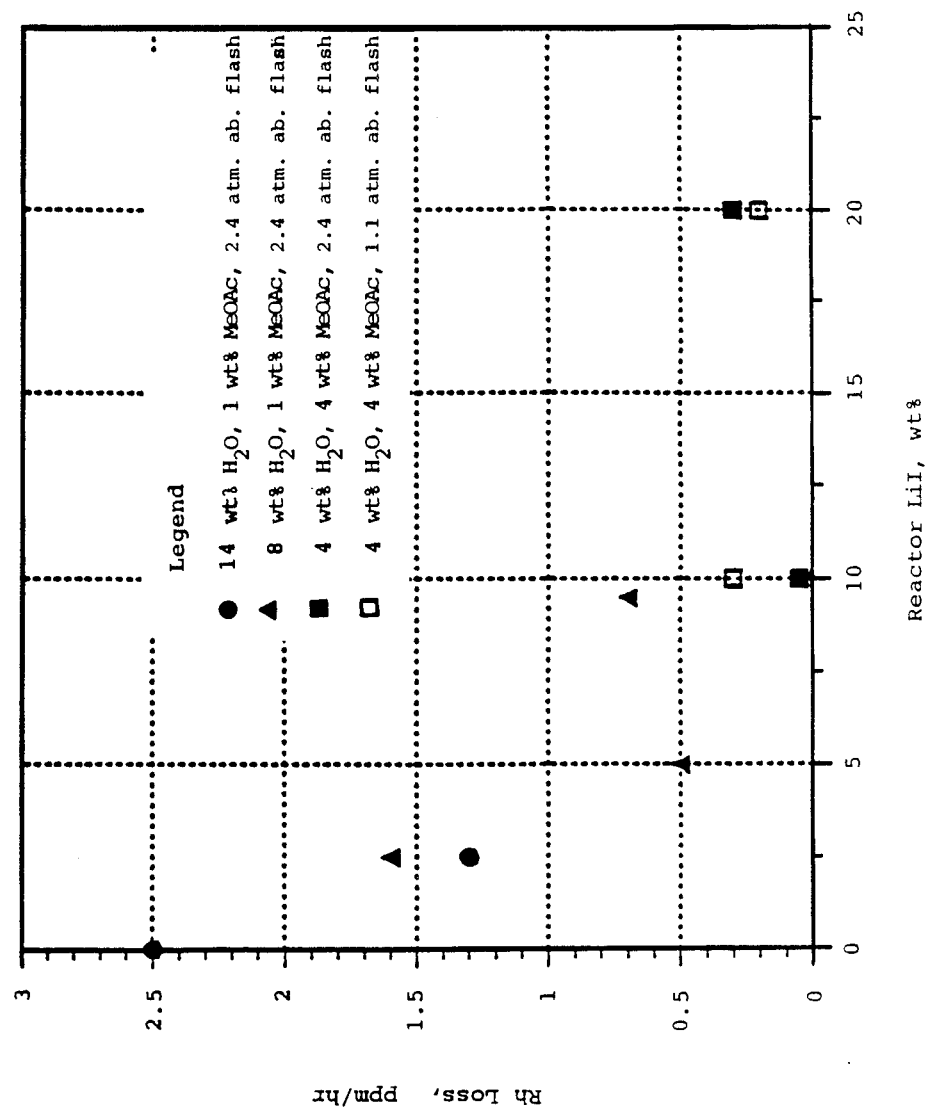
Figure 25:
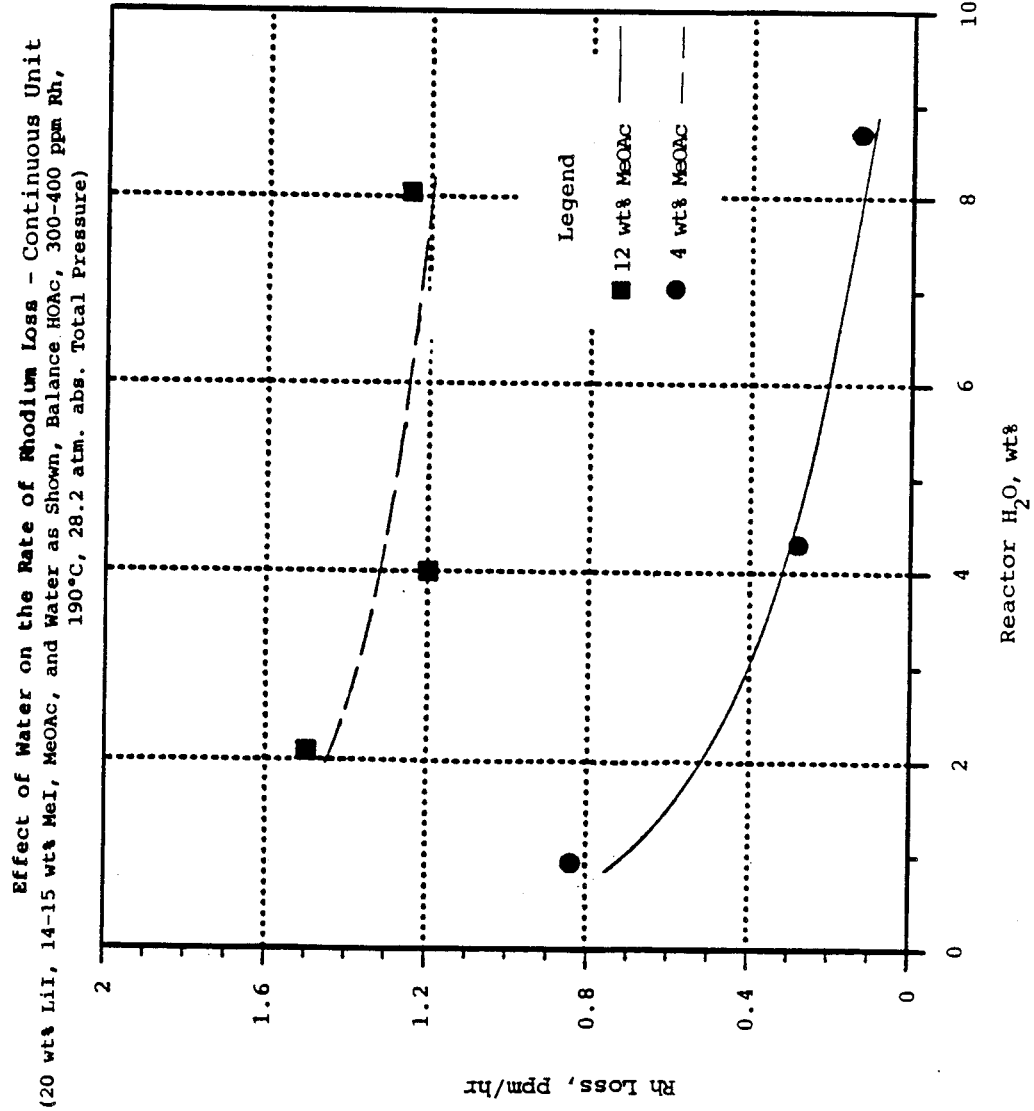

FIGS. 24 and 25 depict the results of studies of rhodium loss from the reaction medium in the continuous unit, FIG. 24 demonstrating that increasing the lithium iodide concentration greatly reduces rhodium loss at varying water concentrations and at two different methyl acetate concentrations while FIG. 25 demonstrates that at higher water concentrations there is less rhodium loss and also that going to the relatively high methyl acetate concentration of 12 wt % increases rhodium loss as compared with using 4 wt % methyl acetate.

The embodiments of the invention in which an exclusive property or privilege is claimed are:

1. In a process for producing acetic acid by reacting methanol with carbon monoxide in a liquid reaction medium containing a rhodium catalyst and comprising water, acetic acid, methyl iodide and methyl acetate and subsequently recovering acetic acid from the resulting reaction product, the improvement which comprises:

maintaining catalyst stability and system productivity by maintaining in said reaction medium during the course of said reaction about 200 ppm to 1000 ppm rhodium catalyst calculated as rhodium, 1.0 to 4 wt % water, 10 to 20 wt % lithium iodide, 12 to 16 wt % methyl iodide and 0.5 to 5 wt % methyl acetate when optimal catalyst stabilization is desired or 2 to 5 wt % methyl acetate when maximal reactor productivity is desired, with the balance consisting essentially of acetic acid.

2. In a process for reacting methanol with carbon monoxide to produce acetic acid in a liquid reaction medium containing a rhodium catalyst in catalytically-effective concentration and consisting essentially of water, acetic acid, methyl iodide, and methyl acetate, and subsequently recovering acetic acid from the resulting reaction product, the improvement which comprises:

maintaining optimal catalyst stability while also maintaining an industrially-satisfactory system productivity by maintaining in said reaction medium during the course of said reaction about 1 to 4 wt % water, 10 to 20 wt % lithium iodide, 0.5 to 5 wt % methyl acetate, and 12 to 16 wt % methyl iodide, with the balance consisting essentially of acetic acid.

3. In a process for reacting methanol with carbon monoxide to produce acetic acid in a liquid reaction medium containing a rhodium catalyst in catalytically-effective concentration and consisting essentially of water, acetic acid, methyl iodide, and methyl acetate, and subsequently recovering acetic acid from the resulting reaction product, the improvement which comprises:

maintaining optimal system productivity while also maintaining an industrially-satisfactory catalyst stability by maintaining in said reaction medium during the course of said reaction about 1 to 4 wt % water, 10 to 20 wt % lithium iodide, 2 to 5 wt % methyl acetate, and 12 to 16 wt % methyl iodide, with the balance consisting essentially of acetic acid.

4. In a process for producing acetic acid by reacting methanol with carbon monoxide in a liquid reaction medium containing a rhodium catalyst and comprising water, acetic acid, methyl iodide and methyl acetate and subsequently recovering acetic acid from the resulting reaction product, the improvement which comprises:

maintaining catalyst stability and system productivity by maintaining in said reaction medium during the course of said reaction about 1 to 4 wt % water, 10 to 20 wt % of a catalyst stabilizer selected from the group consisting of lithium iodide, lithium acetate and mixtures thereof, 12 to 16 wt % of methyl iodide and 0.5 to 5 wt % of methyl acetate when optimal catalyst stabilization is desired or 2 to 5 wt % methyl acetate when optimal reactor productivity is desired, with the balance consisting essentially of acetic acid.

* * * * *